(12) United States Patent
Hodges et al.

(10) Patent No.: US 9,784,707 B2
(45) Date of Patent: Oct. 10, 2017

(54) SYSTEM AND METHOD FOR MEASURING AN ANALYTE IN A SAMPLE

(75) Inventors: Alastair M. Hodges, Blackburn South (AU); Ronald C. Chatelier, Bayswater (AU)

(73) Assignee: LifeScan, Inc., Milpitas, CA (US)

( * ) Notice: Subject to any disclaimer, the term of this patent is extended or adjusted under 35 U.S.C. 154(b) by 0 days.

(21) Appl. No.: 13/620,448

(22) Filed: Sep. 14, 2012

(65) Prior Publication Data
US 2013/0008804 A1    Jan. 10, 2013

Related U.S. Application Data

(62) Division of application No. 12/464,935, filed on May 13, 2009.

(60) Provisional application No. 61/131,572, filed on Jun. 9, 2008.

(51) Int. Cl.
G01N 27/327 (2006.01)

(52) U.S. Cl.
CPC ................. G01N 27/3274 (2013.01)

(58) Field of Classification Search
CPC ................................. G01N 27/3274
USPC ....................................... 205/775
See application file for complete search history.

(56) References Cited

U.S. PATENT DOCUMENTS

| | | |
|---|---|---|
| 3,648,160 A | 3/1972 | Beaver |
| 4,088,448 A | 5/1978 | Lilja et al. |
| 4,224,125 A | 9/1980 | Nakamura et al. |
| 4,233,029 A | 11/1980 | Columbus |
| 4,250,257 A | 2/1981 | Lee et al. |
| 4,254,083 A | 3/1981 | Columbus |
| 4,259,165 A | 3/1981 | Miyake et al. |
| 4,301,412 A | 11/1981 | Hill et al. |
| 4,301,414 A | 11/1981 | Hill et al. |
| 4,303,887 A | 12/1981 | Hill et al. |
| 4,307,188 A | 12/1981 | White |
| 4,374,013 A | 2/1983 | Enfors et al. |
| 4,404,066 A | 9/1983 | Johnson |

(Continued)

FOREIGN PATENT DOCUMENTS

| | | |
|---|---|---|
| AU | 3104293 A | 7/1993 |
| AU | 5487394 | 8/1994 |

(Continued)

OTHER PUBLICATIONS

Canadian Office Action for 2,748,433; dated Aug. 1, 2013; 3 pages.

(Continued)

Primary Examiner — Louis Rufo
(74) Attorney, Agent, or Firm — Barclay Damon, LLP

(57) ABSTRACT

Methods for calculating an analyte concentration of a sample are provided. In one exemplary embodiment the method includes steps that are directed toward accounting for inaccuracies that occur as a result of temperature variations in a sample, a meter, or the surrounding environment. In another exemplary embodiment the method includes steps that are directed toward determining whether an adequate sample is provided in a meter because insufficient samples can result in inaccuracies. The methods that are provided can be incorporated into a variety of mechanisms, but they are primarily directed toward glucose meters for blood samples and toward meters for controls solutions.

14 Claims, 21 Drawing Sheets

(56) References Cited

U.S. PATENT DOCUMENTS

| | | | |
|---|---|---|---|
| 4,431,004 | A | 2/1984 | Bessman et al. |
| 4,436,812 | A | 3/1984 | Endoh et al. |
| 4,508,613 | A | 4/1985 | Busta et al. |
| 4,517,287 | A | 5/1985 | Scheibe et al. |
| 4,517,291 | A | 5/1985 | Seago |
| 4,533,440 | A | 8/1985 | Kim |
| 4,545,382 | A | 10/1985 | Higgins et al. |
| 4,547,735 | A | 10/1985 | Kiesewetter |
| 4,552,840 | A | 11/1985 | Riffer |
| 4,629,563 | A | 12/1986 | Wrasidlo |
| 4,654,197 | A | 3/1987 | Lilja et al. |
| 4,664,119 | A | 5/1987 | Bessman et al. |
| 4,686,479 | A | 8/1987 | Young |
| 4,711,245 | A | 12/1987 | Higgins et al. |
| 4,774,039 | A | 9/1988 | Wrasidlo |
| 4,790,925 | A | 12/1988 | Miller et al. |
| 4,900,424 | A | 2/1990 | Birth et al. |
| 4,919,770 | A | 4/1990 | Preidel et al. |
| 4,963,815 | A | 10/1990 | Hafeman |
| 5,059,908 | A | 10/1991 | Mina |
| 5,064,516 | A | 11/1991 | Rupich |
| 5,089,320 | A | 2/1992 | Straus et al. |
| 5,108,564 | A | 4/1992 | Szuminsky et al. |
| 5,120,420 | A | 6/1992 | Nankai et al. |
| 5,122,244 | A | 6/1992 | Hoenes et al. |
| 5,126,034 | A | 6/1992 | Carter et al. |
| 5,128,015 | A | 7/1992 | Szuminsky et al. |
| 5,141,868 | A | 8/1992 | Shanks et al. |
| 5,151,166 | A | 9/1992 | Harral et al. |
| 5,171,689 | A | 12/1992 | Kawaguri et al. |
| 5,192,415 | A | 3/1993 | Yoshioka et al. |
| 5,229,282 | A | 7/1993 | Yoshioka et al. |
| 5,243,516 | A | 9/1993 | White |
| 5,272,060 | A | 12/1993 | Hamamoto et al. |
| 5,272,087 | A | 12/1993 | El Murr et al. |
| 5,282,950 | A | 2/1994 | Dietze et al. |
| 5,312,590 | A | 5/1994 | Gunasingham et al. |
| 5,320,732 | A | 6/1994 | Nankai et al. |
| 5,352,351 | A | 10/1994 | White et al. |
| 5,382,346 | A | 1/1995 | Uenoyama et al. |
| 5,384,028 | A | 1/1995 | Ito et al. |
| 5,385,846 | A | 1/1995 | Kuhn et al. |
| 5,388,163 | A | 2/1995 | Elko et al. |
| 5,393,399 | A | 2/1995 | Van den Berg et al. |
| 5,395,504 | A | 3/1995 | Saurer et al. |
| 5,405,511 | A | 4/1995 | White et al. ............... 205/777.5 |
| 5,413,690 | A | 5/1995 | Kost et al. |
| 5,437,999 | A | 8/1995 | Diebold et al. |
| 5,469,369 | A | 11/1995 | Rose-Pehrsson et al. |
| 5,508,171 | A | 4/1996 | Walling et al. ............ 205/777.5 |
| 5,508,203 | A | 4/1996 | Fuller |
| 5,509,410 | A | 4/1996 | Hill et al. |
| 5,520,787 | A | 5/1996 | Hanagan et al. |
| 5,527,446 | A | 6/1996 | Kosek et al. |
| 5,567,302 | A | 10/1996 | Song et al. |
| 5,611,908 | A | 3/1997 | Matthiessen et al. |
| 5,620,579 | A | 4/1997 | Genshaw et al. |
| 5,628,890 | A | 5/1997 | Carter et al. |
| 5,642,734 | A | 7/1997 | Ruben |
| 5,645,709 | A | 7/1997 | Birch et al. |
| 5,653,863 | A | 8/1997 | Genshaw et al. |
| 5,660,791 | A | 8/1997 | Brenneman et al. |
| 5,723,284 | A | 3/1998 | Ye |
| 5,762,770 | A | 6/1998 | Pritchard et al. |
| 5,849,174 | A | 12/1998 | Sanghera et al. |
| 5,869,971 | A | 2/1999 | Sherman |
| 5,909,114 | A | 6/1999 | Uchiyama et al. |
| 5,942,102 | A | 8/1999 | Hodges et al. |
| 5,997,817 | A | 12/1999 | Crismore et al. |
| 6,058,934 | A | 5/2000 | Sullivan |
| 6,071,391 | A | 6/2000 | Gotoh et al. |
| 6,153,069 | A | 11/2000 | Pottgen et al. |
| 6,179,979 | B1 | 1/2001 | Hodges et al. |
| 6,193,873 | B1 | 2/2001 | Ohara et al. |
| 6,251,260 | B1 | 6/2001 | Heller et al. |
| 6,284,125 | B1 | 9/2001 | Hodges et al. |
| 6,287,451 | B1 | 9/2001 | Winarta et al. |
| 6,379,513 | B1 | 4/2002 | Chambers et al. |
| 6,391,645 | B1 | 5/2002 | Huang et al. ................... 436/95 |
| 6,413,410 | B1 | 7/2002 | Hodges et al. |
| 6,461,496 | B1 | 10/2002 | Feldman et al. |
| 6,475,372 | B1 | 11/2002 | Ohara et al. ............... 205/777.5 |
| 6,503,381 | B1 | 1/2003 | Gotoh et al. |
| 6,576,117 | B1 | 6/2003 | Iketaki et al. |
| 6,595,919 | B2 | 7/2003 | Berner et al. |
| 6,645,368 | B1 | 11/2003 | Beaty et al. |
| 6,676,995 | B2 | 1/2004 | Dick et al. |
| 6,730,200 | B1 | 5/2004 | Stewart et al. |
| 6,749,887 | B1 | 6/2004 | Dick et al. |
| 6,816,537 | B2 | 11/2004 | Liess |
| 6,818,180 | B2 | 11/2004 | Douglas et al. |
| 6,824,670 | B2 | 11/2004 | Tokunaga et al. ............ 205/792 |
| 6,830,934 | B1 | 12/2004 | Harding et al. |
| 6,863,801 | B2 | 3/2005 | Hodges et al. |
| 6,869,411 | B2 | 3/2005 | Langley et al. |
| 6,936,146 | B2 | 8/2005 | Ryu et al. |
| 6,942,770 | B2 | 9/2005 | Cai et al. |
| 7,008,525 | B2 | 3/2006 | Morita et al. |
| 7,018,843 | B2 | 3/2006 | Heller |
| 7,083,712 | B2 | 8/2006 | Morita et al. |
| 7,122,111 | B2 | 10/2006 | Tokunaga et al. |
| 7,132,041 | B2 | 11/2006 | Deng et al. |
| 7,160,251 | B2 | 1/2007 | Neel et al. |
| 7,199,594 | B2 * | 4/2007 | Kermani ...................... 324/663 |
| 7,201,042 | B2 | 4/2007 | Yamaoka et al. |
| 7,338,639 | B2 | 3/2008 | Burke et al. |
| 7,390,667 | B2 | 6/2008 | Burke |
| 7,407,811 | B2 | 8/2008 | Burke |
| 7,452,457 | B2 | 11/2008 | Burke |
| 7,488,601 | B2 | 2/2009 | Burke |
| 7,494,816 | B2 | 2/2009 | Burke |
| 7,504,020 | B2 | 3/2009 | Tokunaga et al. |
| 7,597,793 | B2 | 10/2009 | Burke |
| 7,604,721 | B2 | 10/2009 | Groll |
| 7,645,373 | B2 | 1/2010 | Groll |
| 7,645,421 | B2 | 1/2010 | Groll |
| 7,718,439 | B2 | 5/2010 | Groll |
| 7,727,467 | B2 | 6/2010 | Burke |
| 7,749,371 | B2 | 7/2010 | Guo et al. |
| 7,749,437 | B2 | 7/2010 | Mosoiu |
| 7,829,023 | B2 | 11/2010 | Burke |
| 7,879,618 | B2 | 2/2011 | Mosoiu |
| 7,892,849 | B2 | 2/2011 | Burke |
| 7,923,258 | B2 | 4/2011 | Heller |
| 7,927,882 | B2 | 4/2011 | Heller |
| 7,955,492 | B2 | 6/2011 | Fujiwara |
| 7,972,861 | B2 | 7/2011 | Deng |
| 7,977,112 | B2 | 7/2011 | Burke |
| 7,981,363 | B2 | 7/2011 | Burke |
| 2002/0139692 | A1 | 10/2002 | Tokunaga et al. |
| 2003/0036202 | A1 | 2/2003 | Teodorcyzk et al. |
| 2003/0098233 | A1 * | 5/2003 | Kermani et al. ............. 204/400 |
| 2003/0109798 | A1 | 6/2003 | Kermani |
| 2004/0005716 | A9 | 1/2004 | Beaty |
| 2004/0079652 | A1 | 4/2004 | Vreeke et al. |
| 2004/0120848 | A1 | 6/2004 | Teodorczyk |
| 2004/0154932 | A1 | 8/2004 | Deng et al. |
| 2004/0182703 | A1 | 9/2004 | Bell et al. |
| 2004/0219624 | A1 | 11/2004 | Teodorcyzk et al. |
| 2004/0235178 | A1 | 11/2004 | Tokunaga et al. |
| 2004/0256248 | A1 | 12/2004 | Burke et al. |
| 2004/0260511 | A1 | 12/2004 | Burke et al. |
| 2005/0036906 | A1 | 2/2005 | Nakahara |
| 2005/0045476 | A1 | 3/2005 | Neel et al. |
| 2005/0153457 | A1 | 7/2005 | Patel et al. |
| 2005/0161344 | A1 * | 7/2005 | Kermani et al. .......... 205/777.5 |
| 2005/0247562 | A1 | 11/2005 | Tokunaga et al. |
| 2005/0284758 | A1 | 12/2005 | Funke |
| 2006/0108236 | A1 | 5/2006 | Kasielke et al. |
| 2006/0231418 | A1 * | 10/2006 | Harding et al. ............. 205/775 |
| 2006/0231421 | A1 | 10/2006 | Diamond et al. |
| 2006/0231423 | A1 * | 10/2006 | Harding et al. ............. 205/792 |
| 2006/0231425 | A1 | 10/2006 | Harding et al. |
| 2007/0000777 | A1 | 1/2007 | Ho et al. |

(56) References Cited

U.S. PATENT DOCUMENTS

| | | | |
|---|---|---|---|
| 2007/0017824 | A1 | 1/2007 | Rippeth et al. |
| 2007/0074977 | A1* | 4/2007 | Guo et al. .............. 205/792 |
| 2007/0102292 | A1 | 5/2007 | Dreibholz et al. |
| 2007/0227912 | A1 | 10/2007 | Chatelier et al. |
| 2007/0235346 | A1 | 10/2007 | Popovich et al. |
| 2007/0235347 | A1* | 10/2007 | Chatelier et al. ........ 205/792 |
| 2007/0256943 | A1 | 11/2007 | Popovich |
| 2008/0083618 | A1 | 4/2008 | Neel et al. |
| 2009/0014339 | A1 | 1/2009 | Beer et al. |
| 2009/0084687 | A1 | 4/2009 | Chatelier et al. |
| 2009/0099787 | A1 | 4/2009 | Carpenter |
| 2009/0184004 | A1 | 7/2009 | Chatelier et al. |
| 2009/0301899 | A1 | 12/2009 | Hodges |
| 2010/0089775 | A1 | 4/2010 | Chen |
| 2010/0170807 | A1 | 7/2010 | Diebold |
| 2010/0206749 | A1 | 8/2010 | Choi |
| 2010/0276303 | A1 | 11/2010 | Fujiwara |
| 2011/0011752 | A1 | 1/2011 | Chatelier et al. |
| 2011/0297554 | A1 | 12/2011 | Wu |
| 2011/0301857 | A1 | 12/2011 | Huang |

FOREIGN PATENT DOCUMENTS

| | | |
|---|---|---|
| AU | 2007201377 | 8/2009 |
| AU | 2009200097 | 1/2011 |
| AU | 2009202200 | 1/2011 |
| CA | 2748433 | 9/2007 |
| CA | 2582643 | 10/2011 |
| CN | 1338049 A | 2/2002 |
| CN | 1692277 A | 11/2005 |
| DE | 3103464 | 8/1982 |
| EP | 0171375 A1 | 2/1986 |
| EP | 0172969 A2 | 3/1986 |
| EP | 0251915 | 1/1988 |
| EP | 0255291 A1 | 2/1988 |
| EP | 0266204 | 5/1988 |
| EP | 0278647 | 8/1988 |
| EP | 0290770 A2 | 11/1988 |
| EP | 0299779 | 1/1989 |
| EP | 0351516 | 1/1990 |
| EP | 0351891 A2 | 1/1990 |
| EP | 0351892 A2 | 1/1990 |
| EP | 0359831 A1 | 3/1990 |
| EP | 0400918 | 12/1990 |
| EP | 0418404 | 3/1991 |
| EP | 0451981 A2 | 10/1991 |
| EP | 0560336 A1 | 9/1993 |
| EP | 0800086 A1 | 10/1997 |
| EP | 1 042 667 A1 | 10/2000 |
| EP | 1156324 A1 | 11/2001 |
| EP | 1172649 A1 | 1/2002 |
| EP | 1281960 A2 | 2/2003 |
| EP | 1 394 545 A1 | 3/2004 |
| EP | 1447452 A1 | 8/2004 |
| EP | 1 455 182 A1 | 9/2004 |
| EP | 1557662 A1 | 7/2005 |
| EP | 1 775 587 A2 | 4/2007 |
| EP | 1839571 A1 | 10/2007 |
| EP | 1840219 A1 | 10/2007 |
| EP | 2098857 | 12/2009 |
| EP | 2267149 | 12/2010 |
| EP | 2076168 | 1/2012 |
| GB | 2020424 | 11/1979 |
| GB | 2154735 | 9/1985 |
| GB | 2201248 | 8/1988 |
| GB | 2235050 | 2/1991 |
| JP | 3099254 | 4/1991 |
| JP | 3167464 | 7/1991 |
| JP | 4066112 | 3/1992 |
| JP | 4343065 A | 11/1992 |
| JP | 5002007 A | 1/1993 |
| JP | 6222874 | 8/1994 |
| JP | 11230934 A | 8/1999 |
| JP | 2001-066274 A | 3/2001 |
| JP | 200166274 | 3/2001 |
| JP | 2001153839 A | 6/2001 |
| JP | 2003114214 | 4/2003 |
| JP | 2003-185615 | 7/2003 |
| JP | 2003-185615 A | 7/2003 |
| JP | 2003-521708 | 7/2003 |
| JP | 2003521708 A | 7/2003 |
| JP | 2003-240747 A | 8/2003 |
| JP | 2003240747 | 8/2003 |
| JP | 2003-262604 | 9/2003 |
| JP | 2004-245836 | 9/2004 |
| JP | 2004245836 A | 9/2004 |
| JP | 2005147990 A | 6/2005 |
| JP | 2005-147990 | 9/2005 |
| JP | 2007-108171 | 4/2007 |
| JP | 2007087710 | 4/2007 |
| JP | 2007108171 A | 4/2007 |
| JP | 2007133985 | 5/2007 |
| JP | 2007522449 | 8/2007 |
| JP | 2007225619 | 9/2007 |
| JP | 2007248281 | 9/2007 |
| JP | 2007-271623 | 10/2007 |
| JP | 2007271623 | 10/2007 |
| JP | 2007-531877 | 11/2007 |
| JP | 2007531877 | 11/2007 |
| JP | 2009528540 | 8/2009 |
| JP | 2009-536744 A | 10/2009 |
| SU | 1351627 | 11/1987 |
| WO | WO-8908713 A1 | 9/1989 |
| WO | WO 91/09373 | 6/1991 |
| WO | WO-9215701 A1 | 9/1992 |
| WO | WO-9402842 A1 | 2/1994 |
| WO | WO-9516198 A1 | 6/1995 |
| WO | WO-9700441 A1 | 1/1997 |
| WO | WO-9718465 A1 | 5/1997 |
| WO | WO-0020626 A1 | 4/2000 |
| WO | 01/40787 A1 | 6/2001 |
| WO | WO 01/57510 A3 | 8/2001 |
| WO | WO-0157510 A2 | 8/2001 |
| WO | 2004040286 A1 | 5/2004 |
| WO | WO2004113913 | 12/2004 |
| WO | WO 2005/008231 A1 | 1/2005 |
| WO | WO2005066355 | 7/2005 |
| WO | 2005098424 A1 | 10/2005 |
| WO | WO 2005/098424 A1 | 10/2005 |
| WO | WO 2005098424 A1 | 10/2005 |
| WO | WO 2006/109280 A2 | 10/2006 |
| WO | WO-2006110504 A1 | 10/2006 |
| WO | WO 2007/040913 A1 | 4/2007 |
| WO | WO2006109277 | 4/2007 |
| WO | 2007/133985 A2 | 11/2007 |
| WO | 2007130907 A2 | 11/2007 |
| WO | WO 2007/131036 A1 | 11/2007 |
| WO | WO 2008/004565 A1 | 1/2008 |

OTHER PUBLICATIONS

Chinese Office Action and Search Report for CN 200810175601.0; dated Mar. 20, 2013; 7 pages.
EP Examination Report for EP 09 250 133,7; dated May 16, 2013; 4 pages.
EP Examination Report for EP 12 164 561,8; dated May 2, 2013; 2 pages.
AU Examination Report for 2012201912; dated Jan. 11, 2013; 4 pages.
AU Examination Report for 2012201916; dated Jan. 24, 2013; 4 pages.
AU Examination Report for 2009227823; dated Feb. 18, 2013; 3 pages.
JP Office Action for 2012-261693; dated Feb. 5, 2013; 2 pages.
EP report for 07251388 dated Jun. 5, 2012.
EP report for 08253148 dated Jun. 4, 2012.
EP report for 10178905 dated Jun. 8, 2012.
EP report for 10178982 dated Jun. 5, 2012.
Wikipedia; Hematocrit; Retrieved on May 24, 2012 (3 pages).
EP report for 12164561 dated Jul. 4, 2012.
Schmidt, "New Principles of amperometric enzyme electrodes . . . " Sensors and Actuators B; vol. 13, No. 1-3, May 1, 1993.

(56) References Cited

OTHER PUBLICATIONS

EP report for 12173292 dated Sep. 12, 2012.
EP report for 12173297 dated Sep. 14, 2012.
EP report for 12173284 dated Sep. 7, 2012.
JP report for 2012076986 dated Sep. 4, 2012.
Cha, Kichul, et al., An electronic method for rapid measurement of haematocrit in blood samples; Physiol Meas, 1994.
CN report for 200910134602 dated Aug. 17, 2012.
JP report for 2009137856 dated Jul. 31, 2012.
EP report for 09251507.1 dated Sep. 13, 2012.
AU report on 2009227823 dated Nov. 1, 2012.
SG report for 200900312-0 dated Oct. 11, 2012.
Chinese Office Action for CN Application No. 200810175601.0; mailed Jul. 4, 2012; 4 pages.
Japanese Office Action for JP Application No. 2009-137856; mailed Jul. 31, 2012; 3 pages.
Japanese Office Action for JP Application No. 2012-076986; mailed Sep. 4, 2012; 3 pages.
Chinese Office Action issued Nov. 22, 2011 for Application No. 200910134602.5 (15 Pages).
Japanese Office Action issued Nov. 29, 2011 for Application No. 2009-006871 (3 Pages).
Japanese Office Action issued Jan. 10, 2012 for Application No. 2011-123761 (3 Pages).
European Extended Search Report for Application No. 07251388.0, dated Jul. 9, 2007, 6 pages.
European Extended Search Report for Application No. EP 09250133, dated Nov. 30, 2009, 10 pages.
European Extended Search Report for Application No. EP 09251507, dated Sep. 14, 2011, 11 pages.
Numerical Recipes: The Art of Scientific Computing, Third Edition. William H. Press et al., Cambridge University Press, Published 2007.
Canadian Examiner's Requisition for Application No. 2648625, dated Apr. 11, 2011, 3 pages.
Japanese Office Action for Application No. JP 2007-087710, mailed Aug. 9, 2011, 2 pages.
Australian Examiner's Report for application No. 2007201377 dated Mar. 19, 2009, 3 pages.
Canadian Examiner's Requisition for application No. 2582643 dated May 19, 2009, 4 pages.
Canadian Examiner's Requisition for application No. 2582643 dated Mar. 10, 2010, 4 pages.
European Examination Report for application No. 07251388.0 dated Apr. 10, 1008, 4 pages.
Australian Examiners Report for application No. 2008221593 dated Mar. 30, 3011, 3 pages.
Canadian Examiners Requisition for application No. 2639776 dated Dec. 21, 2010, 6 pages.
Australian Examiner's Report for application No. 2009200097 dated Jul. 2, 2010, 2 pages.
Australian Examiner's Report for application No. 2011201199 dated May 10, 2011, 2 pages.
European Search Report for application No. 09251507.1 dated May 11, 2011, 5 pages.
European Search Report, Application No. EP 10178982 mailed Nov. 22, 2010.
Japanese Office Action, Application No. JP 2009-006871 mailed Mar. 1, 2011.
European Search Report, Application No. EP 08253148.4 mailed Nov. 24, 2010, 7 pages.
European Search Report, Application No. EP 10178905, dated Nov. 25, 2010, 7 pages.

Australian Search Report for Australian application No. 2008221593, 3 pages.
Australian Examiner's first report on Patent Application No. 2009202200, dated Jul. 22, 2010 (3 pages).
(Abstract Only) Kobayashi Yoshiaki et al., Biosensor. JP 61002060, Jan. 8, 1986.
Laszlo Daruhazi et al. "Cyclic Voltammetry for Reversible Redox-Electrode Reactions in Thin-Layer Cells With Closely Separated Working and Auxiliary Electrodes of the Same Size" in J. Electroanal. Chem., 264:77-89 (1989).
Osamu, Niwa, et al., "Electrochemical Behavior of Redox Species at Interdigitated Array Electrodes with Different Geometries: Consideration of Redox Cycling and Collection Efficiency," Analytical Chemistry; Mar. 1990, vol. 62, No. 5, pp. 447-452.
Australian Examiner's first report on Patent Application No. 2007201377, dated Jun. 25, 2008.
European Search Report, Application No. EP 09250133, mailed Sep. 15, 2009.
Australian Patent Examination Report for AU 2013202708; dated Feb. 18, 2014 (6 pages).
Australian Patent Examination Report for AU 2013202716; dated Feb. 28, 2014 (3 pages).
Australian Patent Examination Report for AU 2013202702; dated Mar. 11, 2014 (6 pages).
Japanese Office Action for JP 2013-129601; dated Mar. 11, 2014 (2 pages).
Chinese Office Action for CN 200810175601.0; dated Nov. 28, 2013 (6 pages).
Japanese Office Action for JP 2012-261693; dated Feb. 12, 2014 (5 pages).
Canadian Office Action for CA 2,668,237; dated Jun. 4, 2014 (3 pages).
Indian Examination Report for IN 1627/KOL/2008; dated Mar. 27, 2013 (2 pages).
Japanese Office Action for JP 2012-261693; Dated: Sep. 2, 2014; 2 pages.
Chinese Office Action and Search Report for CN 201310139029.3; Dated Sep. 3, 2014; 10 pages.
Canadian Office Action for CA 2,748,433; Dated Nov. 3, 2014; 5 pages.
European Office Action for EP 09 250 133.7; dated: Nov. 17, 2014; 2 pages.
Japanese Office Action for JP 2014-098994; dated: Jan. 13, 2015; 2 pages.
Japanese Office Action for JP 2012-261693; dated: Mar. 24, 2015; 2 pages.
Australian Examination Report for AU 2013263743; dated: Mar. 25, 2015; 4 pages.
Canadian Office Action and Search Report for CA 2,648,625; dated: Apr. 7, 2015 (5 pages).
Singapore Search Report and Written Opinion for SG 2013028881; dated: Nov. 21, 2014 and Mar. 11, 2015; (21 pages).
Japanese Office Action for JP 2014-098994; Dated: Sep. 1, 2015; 2 pages.
European Office Action for EP 09 251 507.1; Dated: Jun. 17, 2016; 4 pages.
Japanese Office Action for JP 2015-234775; dated: Nov. 29, 2016; 2 pages.
European Examination Report for EP 09 251 507.1; dated Feb. 3, 2017; 2 pages.
Japanese Office Action for JP 2015-234775; dated: Jul. 4, 2017; 2 pages.

* cited by examiner

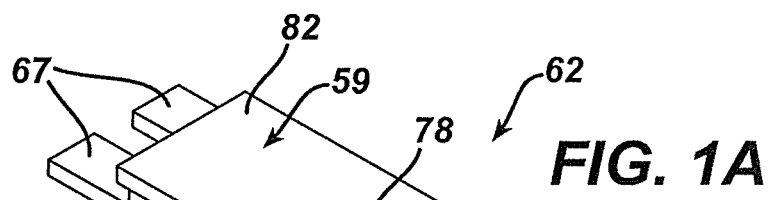
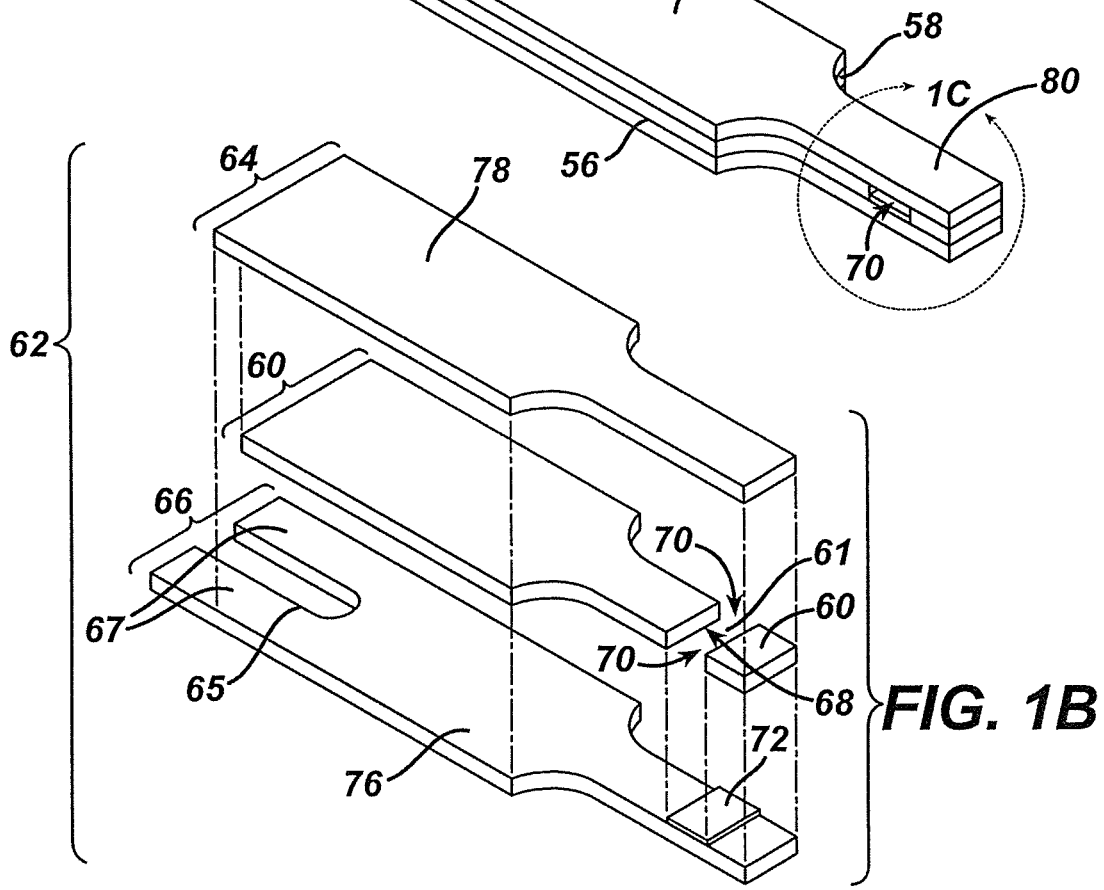
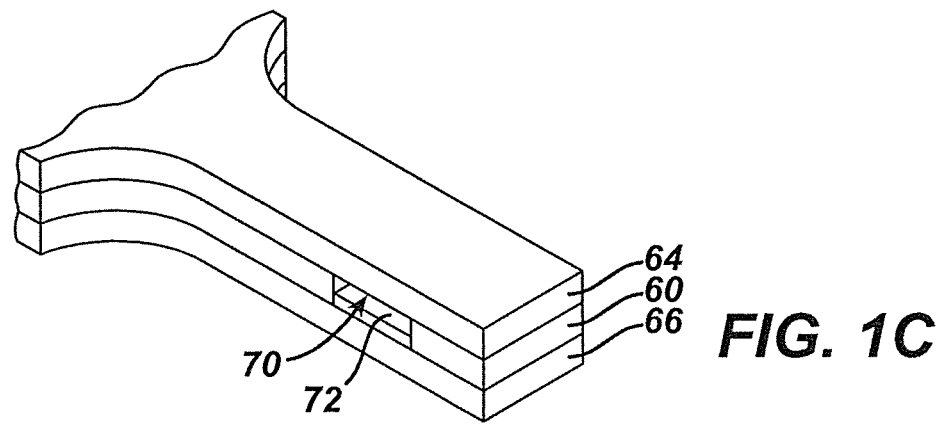

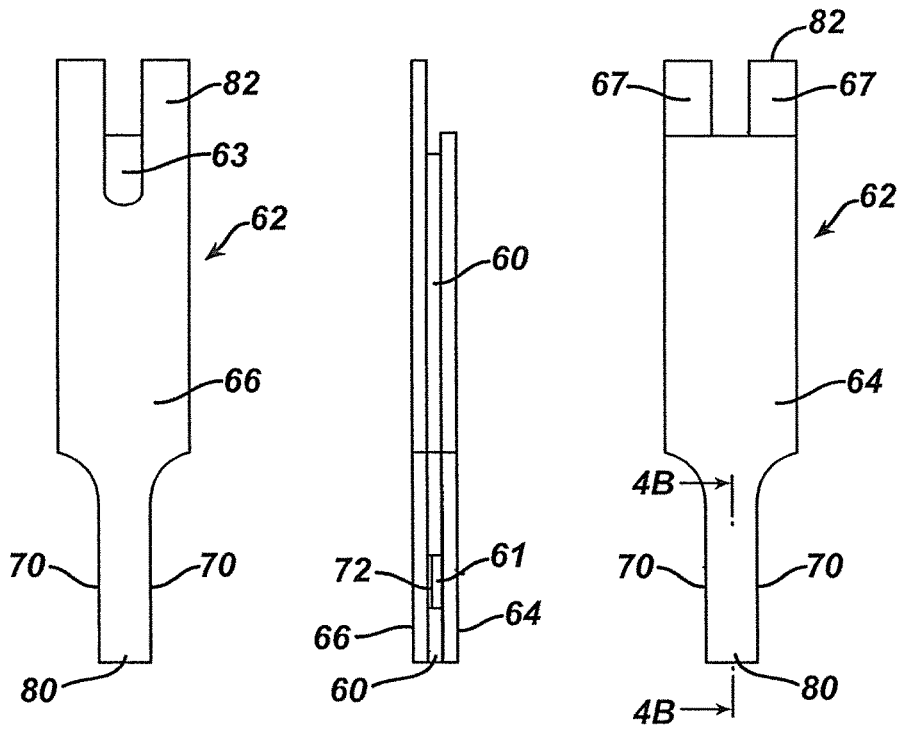
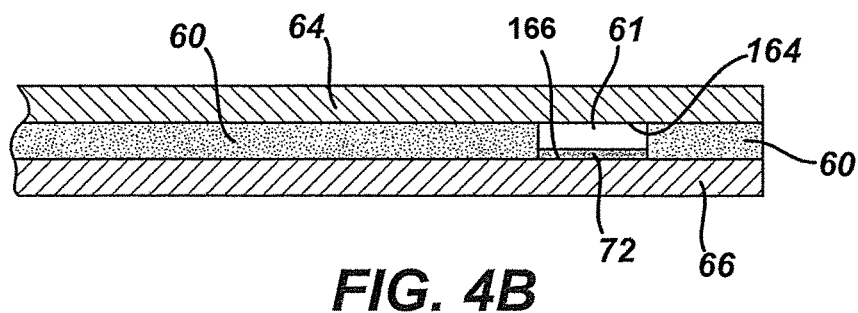

SYSTEM AND METHOD FOR MEASURING AN ANALYTE IN A SAMPLE

RELATED APPLICATION(S)

This application is a divisional application of U.S. patent application Ser. No. 12/464,935, entitled: "System and Method for Measuring an Analyte in a Sample", filed on May 13, 2009, which claims priority to U.S. Patent Application Ser. No. 61/131,572, entitled "System and Method for Measuring an Analyte in a Sample" filed on Jun. 9, 2008, which is hereby incorporated by reference in its entirety. This application is also related to the following co-pending patent applications: U.S. Patent Application Publication No. 2007/0235347, entitled "Systems and Methods for Discriminating Control Solution from a Physiological Sample" and filed on Mar. 31, 2006; U.S. Patent Application Publication No. 2009/0084687, entitled "Systems and Methods of Discriminating Control Solution From a Physiological Sample" and filed on Sep. 16, 2008, and U.S. patent application Ser. No. 12/349,017, entitled "System and Method For Measuring an Analyte in a Sample" filed on Jan. 6, 2009, each of which is hereby incorporated by reference in its entirety.

FIELD

The present disclosure relates to methods and systems for determining analyte concentration of a sample.

BACKGROUND

Analyte detection in physiological fluids, e.g. blood or blood derived products, is of ever increasing importance to today's society. Analyte detection assays find use in a variety of applications, including clinical laboratory testing, home testing, etc., where the results of such testing play a prominent role in diagnosis and management in a variety of disease conditions. Analytes of interest include glucose for diabetes management, cholesterol, and the like. In response to this growing importance of analyte detection, a variety of analyte detection protocols and devices for both clinical and home use have been developed.

One type of method that is employed for analyte detection is an electrochemical method. In such methods, an aqueous liquid sample is placed into a sample-receiving chamber in an electrochemical cell that includes two electrodes, e.g., a counter and working electrode. The analyte is allowed to react with a redox reagent to form an oxidizable (or reducible) substance in an amount corresponding to the analyte concentration. The quantity of the oxidizable (or reducible) substance present is then estimated electrochemically and related to the amount of analyte present in the initial sample.

Such systems are susceptible to various modes of inefficiency and/or error. For example, variations in temperatures can affect the results of the method. This is especially relevant when the method is carried out in an uncontrolled environment, as is often the case in home applications or in third world countries. Errors can also occur when the sample size is insufficient to get an accurate result. Partially filled test strips can potentially give an inaccurate result because the measured test currents are proportional to the area of the working electrode that is wetted with sample. Thus, partially filled test strips can under certain conditions provide a glucose concentration that is negatively biased. A user can have difficulty determining whether an electrode area of a test strip is completely covered by a sample. Many test strips, including the ones described herein, have a relatively small volume (<one microliter) making it difficult for a user to see and judge whether there is a small area of an electrode that is unwetted. This can especially be a problem for people with diabetes that often have poor visual acuity.

SUMMARY

Various aspects of a method of calculating an analyte concentration of a sample are provided. In one aspect the method accounts for temperature variation and includes applying a sample to a test strip and applying a first test voltage for a first time interval between a first electrode and a second electrode sufficient to oxidize a reduced mediator at the second electrode. A second test voltage can be applied for a second time interval between the first electrode and the second electrode that is also sufficient to oxidize the reduced mediator at the first electrode. A first glucose concentration can be calculated based on the test current values during the first time interval and the second time interval. Additionally, the test meter can measure a temperature value. Accordingly, a temperature corrected glucose concentration can be calculated based on the first glucose concentration and the temperature value.

In another aspect of a method of calculating an analyte concentration of a sample, the method is configured to determine whether a test strip is sufficiently filled with a sample. The method includes applying a first test voltage between a first electrode and a second electrode of a test strip. The first test voltage can have both an AC voltage component and a DC voltage component. The AC voltage component can be applied at a predetermined amount of time after the application of the first test voltage. The DC voltage component can have a magnitude sufficient to cause a limiting test current at the second electrode. Accordingly, a portion of the resulting test current from the AC voltage component can be processed into a capacitance value.

BRIEF DESCRIPTION OF THE DRAWINGS

The present disclosure will be more fully understood from the following detailed description taken in conjunction with the accompanying drawings, in which:

FIG. 1A is a perspective view of a test strip;

FIG. 1B is an exploded perspective view of the test strip of FIG. 1A;

FIG. 1C is a perspective view of a distal portion of the test strip of FIG. 1A;

FIG. 2 is a bottom plan view of the test strip of FIG. 1A;

FIG. 3 is a side plan view of the test strip of FIG. 1A;

FIG. 4A is a top plan view of the test strip of FIG. 1A;

FIG. 4B is a partial side view of the distal portion of the test strip consistent with arrows 4B-4B of FIG. 4A;

DETAILED DESCRIPTION

Figure 5:
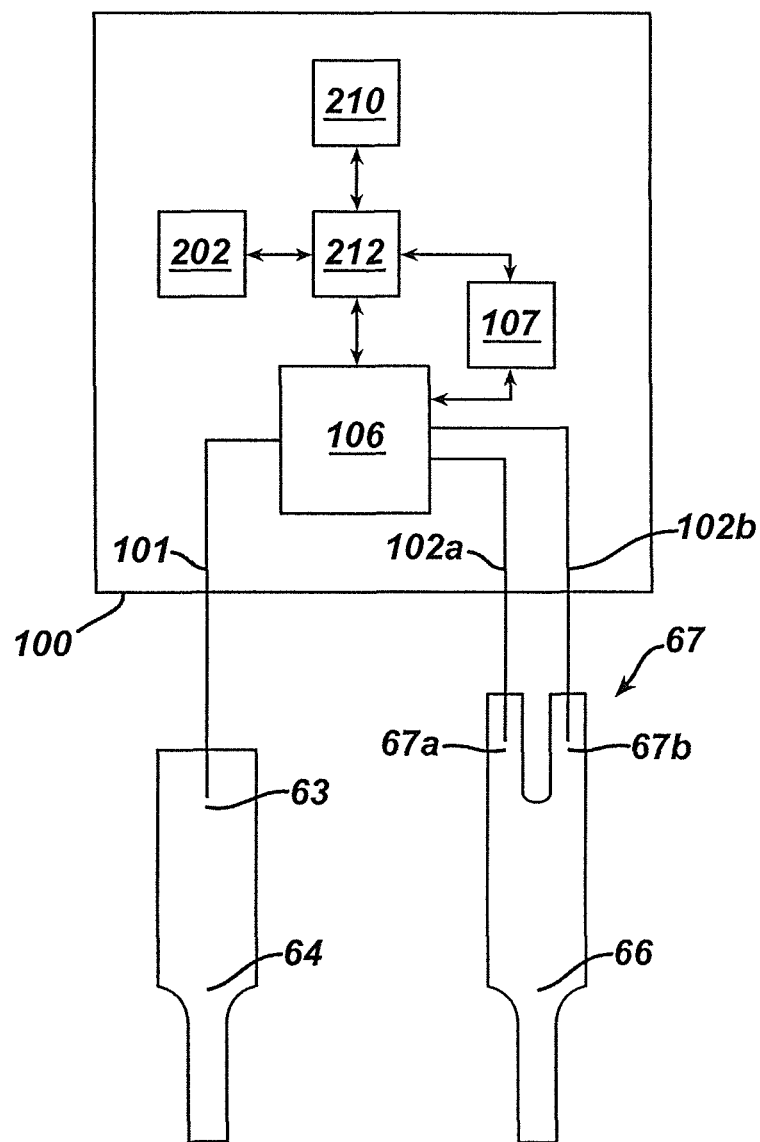
FIG. 5 is a simplified schematic showing a test meter electrically interfacing with the test strip contact pads.

Certain exemplary embodiments will now be described to provide an overall understanding of the principles of the structure, function, manufacture, and use of the devices, systems, and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

The subject systems and methods are suitable for use in the determination of a wide variety of analytes in a wide variety of samples, and are particularly suited for use in the determination of analytes in whole blood, plasma, serum, interstitial fluid, or derivatives thereof. In an exemplary embodiment, a glucose test system based on a thin-layer cell design with opposing electrodes and tri-pulse electrochemical detection that is fast (e.g., about 5 second analysis time), requires a small sample (e.g., about 0.4 µL), and can provide improved reliability and accuracy of blood glucose measurements. In the reaction cell, glucose in the sample can be oxidized to gluconolactone using glucose dehydrogenase and an electrochemically active mediator can be used to shuttle electrons from the enzyme to a palladium working electrode. A potentiostat can be utilized to apply a tri-pulse potential waveform to the working and counter electrodes, resulting in test current transients used to calculate the glucose concentration. Further, additional information gained from the test current transients may be used to discriminate between sample matrices and correct for variability in blood samples due to hematocrit, temperature variation, electrochemically active components, and identify possible system errors.

The subject methods can be used, in principle, with any type of electrochemical cell having spaced apart first and second electrodes and a reagent layer. For example, an electrochemical cell can be in the form of a test strip. In one aspect, the test strip may include two opposing electrodes separated by a thin spacer for defining a sample-receiving chamber or zone in which a reagent layer is located. One skilled in the art will appreciate that other types of test strips, including, for example, test strips with co-planar electrodes may also be used with the methods described herein.

FIGS. 1A to 4B show various views of an exemplary test strip 62 suitable for use with the methods and systems described herein. In an exemplary embodiment, a test strip 62 is provided which includes an elongate body extending from a distal end 80 to a proximal end 82, and having lateral edges 56, 58, as illustrated in FIG. 1A. As shown in FIG. 1B, the test strip 62 also includes a first electrode layer 66, a second electrode layer 64, and a spacer 60 sandwiched in between the two electrode layers 64 and 66. The first electrode layer 66 can include a first electrode 166, a first connection track 76, and a first contact pad 67, where the first connection track 76 electrically connects the first electrode 166 to the first contact pad 67, as shown in FIGS. 1B and 4B. Note that the first electrode 166 is a portion of the first electrode layer 66 that is immediately underneath the reagent layer 72, as indicated by FIGS. 1B and 4B. Similarly, the second electrode layer 64 can include a second electrode 164, a second connection track 78, and a second contact pad 63, where the second connection track 78 electrically connects the second electrode 164 with the second contact pad 63, as shown in FIGS. 1B, 2, and 4B.

Note that the second electrode 164 is a portion of the second electrode layer 64 that is above the reagent layer 72, as indicated by FIG. 4B.

As shown, the sample-receiving chamber 61 is defined by the first electrode 166, the second electrode 164, and the spacer 60 near the distal end 80 of the test strip 62, as shown in FIGS. 1B and 4B. The first electrode 166 and the second electrode 164 can define the bottom and the top of sample-receiving chamber 61, respectively, as illustrated in FIG. 4B. A cutout area 68 of the spacer 60 can define the sidewalls of the sample-receiving chamber 61, as illustrated in FIG. 4B. In one aspect, the sample-receiving chamber 61 can include ports 70 that provide a sample inlet and/or a vent, as shown in FIGS. 1A to 1C. For example, one of the ports can allow a fluid sample to ingress and the other port can allow air to egress.

In an exemplary embodiment, the sample-receiving chamber 61 can have a small volume. For example, the chamber 61 can have a volume in the range of from about 0.1 microliters to about 5 microliters, about 0.2 microliters to about 3 microliters, or, preferably, about 0.3 microliters to about 1 microliter. To provide the small sample volume, the cutout 68 can have an area ranging from about 0.01 $cm^2$ to about 0.2 $cm^2$, about 0.02 $cm^2$ to about 0.15 $cm^2$, or, preferably, about 0.03 $cm^2$ to about 0.08 $cm^2$. In addition, first electrode 166 and second electrode 164 can be spaced apart in the range of about 1 micron to about 500 microns, preferably between about 10 microns and about 400 microns, and more preferably between about 40 microns and about 200 microns. The relatively close spacing of the electrodes can also allow redox cycling to occur, where oxidized mediator generated at first electrode 166, can diffuse to second electrode 164 to become reduced, and subsequently diffuse back to first electrode 166 to become oxidized again. Those skilled in the art will appreciate that various such volumes, areas, and/or spacing of electrodes is within the spirit and scope of the present disclosure.

In one embodiment, the first electrode layer 66 and the second electrode layer 64 can be a conductive material formed from materials such as gold, palladium, carbon, silver, platinum, tin oxide, iridium, indium, or combinations thereof (e.g., indium doped tin oxide). In addition, the electrodes can be formed by disposing a conductive material onto an insulating sheet (not shown) by a sputtering, electroless plating, or a screen-printing process. In one exemplary embodiment, the first electrode layer 66 and the second electrode layer 64 can be made from sputtered palladium and sputtered gold, respectively. Suitable materials that can be employed as spacer 60 include a variety of insulating materials, such as, for example, plastics (e.g., PET, PETG, polyimide, polycarbonate, polystyrene), silicon, ceramic, glass, adhesives, and combinations thereof. In one embodiment, the spacer 60 may be in the form of a double sided adhesive coated on opposing sides of a polyester sheet where the adhesive may be pressure sensitive or heat activated. Those skilled in the art will appreciate that various other materials for the first electrode layer 66, the second electrode layer 64, and/or the spacer 60 are within the spirit and scope of the present disclosure.

Various mechanisms and/or processes can be utilized to dispose a reagent layer 72 within the sample-receiving chamber 61. For example, the reagent layer 72 can be disposed within the sample-receiving chamber 61 using a process such as slot coating, dispensing from the end of a tube, ink jetting, and screen printing. In one embodiment, the reagent layer 72 can include at least a mediator and an enzyme and is deposited onto first electrode 166. Examples of suitable mediators include ferricyanide, ferrocene, ferrocene derivatives, osmium bipyridyl complexes, and quinone derivatives. Examples of suitable enzymes include glucose oxidase, glucose dehydrogenase (GDH) using a pyrroloquinoline quinone (PQQ) co-factor, GDH using a nicotinamide adenine dinucleotide (NAD) co-factor, and GDH using a flavin adenine dinucleotide (FAD) co-factor [E.C.1.1.99.10]. The reagent layer 72 can be prepared from a formulation that contains 33 mM potassium citraconate, pH 6.8, 0.033% Pluronic P103, 0.017% Pluronic F87, 0.85 mM $CaCl_2$, 30 mM sucrose, 286 µM PQQ, 15 mg/mL apo-GDH, and 0.6 M ferricyanide. Alternatively, the PQQ can be left out of the formulation and the apo-GDH can be replaced with FAD-GDH. Pluronics are block copolymers based on ethylene oxide and propylene oxide, which can function as antifoaming agents and/or wetting agents.

The formulation can be applied at 570 µL/min using a 13 gauge needle poised about 150 µm above a palladium web moving at about 10 m/min. Alternatively, the concentration of the solids in the reagent can be increased by 50% and the flow rate can be reduced to 380 µL/min in order to maintain a constant reagent coating density. Before coating the palladium web with the enzyme formulation, it can be coated with 2-mercaptoethane sulfonic acid (MESA). A 95 µm thick spacer with a 1.2 mm wide channel cut in it can be laminated to the reagent layer and the palladium web at 70° C. Next, a MESA-coated gold web can be laminated to the other side of the spacer. The spacer can be made from PET coated on both sides with a thermoplastic such as Vitel, which is a linear saturated copolyester resin having a relatively high molecular weight. The resulting laminate can be cut such that the fill path of the sample-receiving chamber is about 3.5 mm long, thus giving a total volume of about 0.4 µL.

In one embodiment, the reagent layer 72 may have an area larger than the area of the first electrodes 166. As a result a portion of the spacer 60 may overlap and touch the reagent layer 72. The spacer 60 may be configured to form a liquid impermeable seal to the first electrode 166 even though a portion of the reagent layer 72 is between the spacer 60 and the first electrode 166. The spacer 60 may intermingle or partially dissolve a portion of the reagent layer 72 to form a liquid impermeable bond to the first electrode 166 sufficient to define the electrode area for at least the total test time. Under certain circumstances where the reagent layer 72 is not sufficiently dry, the spacer 60 may not be able to form a liquid impermeable seal and, as a result, the liquid may seep between the spacer 60 and the first electrode 166. Such a leakage event may cause an inaccurate glucose measurement to occur.

Either the first electrode 166 or the second electrode 164 can perform the function of a working electrode depending on the magnitude and/or polarity of the applied test voltage. The working electrode may measure a limiting test current that is proportional to the reduced mediator concentration. For example, if the current limiting species is a reduced mediator (e.g., ferrocyanide), then it can be oxidized at the first electrode 166 as long as the test voltage is sufficiently greater than the redox mediator potential with respect to the second electrode 164. In such a situation, the first electrode 166 performs the function of the working electrode and the second electrode 164 performs the function of a counter/reference electrode. Note that one skilled in the art may refer to a counter/reference electrode simply as a reference electrode or a counter electrode. A limiting oxidation occurs when all reduced mediator has been depleted at the working electrode surface such that the measured oxidation current is proportional to the flux of reduced mediator diffusing from the bulk solution towards the working electrode surface. The term bulk solution refers to a portion of the solution sufficiently far away from the working electrode where the reduced mediator is not located within a depletion zone. It should be noted that unless otherwise stated for test strip 62, all potentials applied by test meter 100 will hereinafter be stated with respect to second electrode 164.

Similarly, if the test voltage is sufficiently less than the redox mediator potential, then the reduced mediator can be oxidized at the second electrode 164 as a limiting current. In such a situation, the second electrode 164 performs the function of the working electrode and the first electrode 166 performs the function of the counter/reference electrode.

Initially, performing an analysis can include introducing a quantity of a fluid sample into a sample-receiving chamber 61 via a port 70. In one aspect, the port 70 and/or the sample-receiving chamber 61 can be configured such that capillary action causes the fluid sample to fill the sample-receiving chamber 61. The first electrode 166 and/or second electrode 164 may be coated with a hydrophilic reagent to promote the capillarity of the sample-receiving chamber 61. For example, thiol derivatized reagents having a hydrophilic moiety such as 2-mercaptoethane sulfonic acid may be coated onto the first electrode and/or the second electrode.

FIG. 5 provides a simplified schematic showing a test meter 100 interfacing with a first contact pad 67a, 67b and a second contact pad 63. The second contact pad 63 can be used to establish an electrical connection to the test meter through a U-shaped notch 65, as illustrated in FIG. 2. In one embodiment, the test meter 100 may include a second electrode connector 101, and first electrode connectors (102a, 102b), a test voltage unit 106, a current measurement unit 107, a processor 212, a memory unit 210, and a visual display 202, as shown in FIG. 5. The first contact pad 67 can include two prongs denoted as 67a and 67b. In one exemplary embodiment, the first electrode connectors 102a and 102b separately connect to prongs 67a and 67b, respectively. The second electrode connector 101 can connect to second contact pad 63. The test meter 100 can measure the resistance or electrical continuity between the prongs 67a and 67b to determine whether the test strip 62 is electrically connected to the test meter 100. One skilled in the art will appreciate that the test meter 100 can use a variety of sensors and circuits to determine when the test strip 62 is properly positioned with respect to the test meter 100.

In one embodiment, the test meter 100 can apply a test voltage and/or a current between the first contact pad 67 and the second contact pad 63. Once the test meter 100 recognizes that the strip 62 has been inserted, the test meter 100 turns on and initiates a fluid detection mode. In one embodiment, the fluid detection mode causes test meter 100 to apply a constant current of about 1 microampere between the first electrode 166 and the second electrode 164. Because the test strip 62 is initially dry, the test meter 100 measures a relatively large voltage, which can be limited by the analog-to-digital converter (A/D) within test meter 100. When the fluid sample bridges the gap between the first electrode 166 and the second electrode 164 during the dosing process, the test meter 100 will measure a decrease in measured voltage that is below a predetermined threshold causing test meter 100 to automatically initiate the glucose test.

Figure 6:
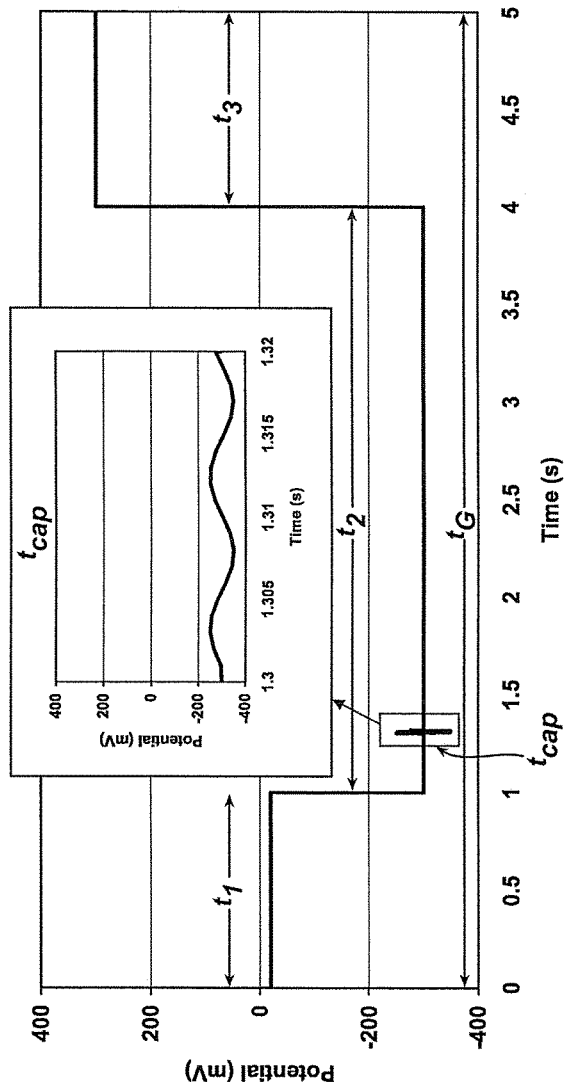
FIG. 6 shows a test voltage waveform in which the test meter applies a plurality of test voltages for prescribed time intervals.

In one embodiment, the test meter 100 can perform a glucose test by applying a plurality of test voltages for prescribed intervals, as shown in FIG. 6. The plurality of test voltages may include a first test voltage $V_1$ for a first time interval $t_1$, a second test voltage $V_2$ for a second time interval $t_2$, and a third test voltage $V_3$ for a third time interval $t_3$. A glucose test time interval $t_G$ represents an amount of time to perform the glucose test (but not necessarily all the calculations associated with the glucose test). Glucose test time interval $t_G$ can range from about 1 second to about 5 seconds. Further, as illustrated in FIG. 6, the second test voltage $V_2$ can include a constant (DC) test voltage component and a superimposed alternating (AC), or oscillating, test voltage component. The superimposed alternating test voltage component can be applied for a time interval indicated by $t_{cap}$. The inset of FIG. 6 magnifies the high frequency AC component.

The plurality of test current values measured during any of the time intervals may be performed at a frequency ranging from about 1 measurement per nanosecond to about one measurement per 100 milliseconds. While an embodiment using three test voltages in a serial manner is described, one skilled in the art will appreciate that the glucose test can include different numbers of open-circuit and test voltages. For example, as an alternative embodiment, the glucose test could include an open-circuit for a first time interval, a second test voltage for a second time interval, and a third test voltage for a third time interval. One skilled in the art will appreciate that names "first," "second," and "third" are chosen for convenience and do not necessarily reflect the order in which the test voltages are applied. For instance, an embodiment can have a potential waveform where the third test voltage can be applied before the application of the first and second test voltage.

Once the glucose assay has been initiated, the test meter 100 may apply a first test voltage $V_1$ (e.g., −20 mV in FIG. 6) for a first time interval $t_1$ (e.g., 1 second in FIG. 6). The first time interval $t_1$ can range from about 0.1 seconds to about 3 seconds and preferably range from about 0.2 seconds to about 2 seconds, and most preferably range from about 0.3 seconds to about 1 seconds.

Figure 7:
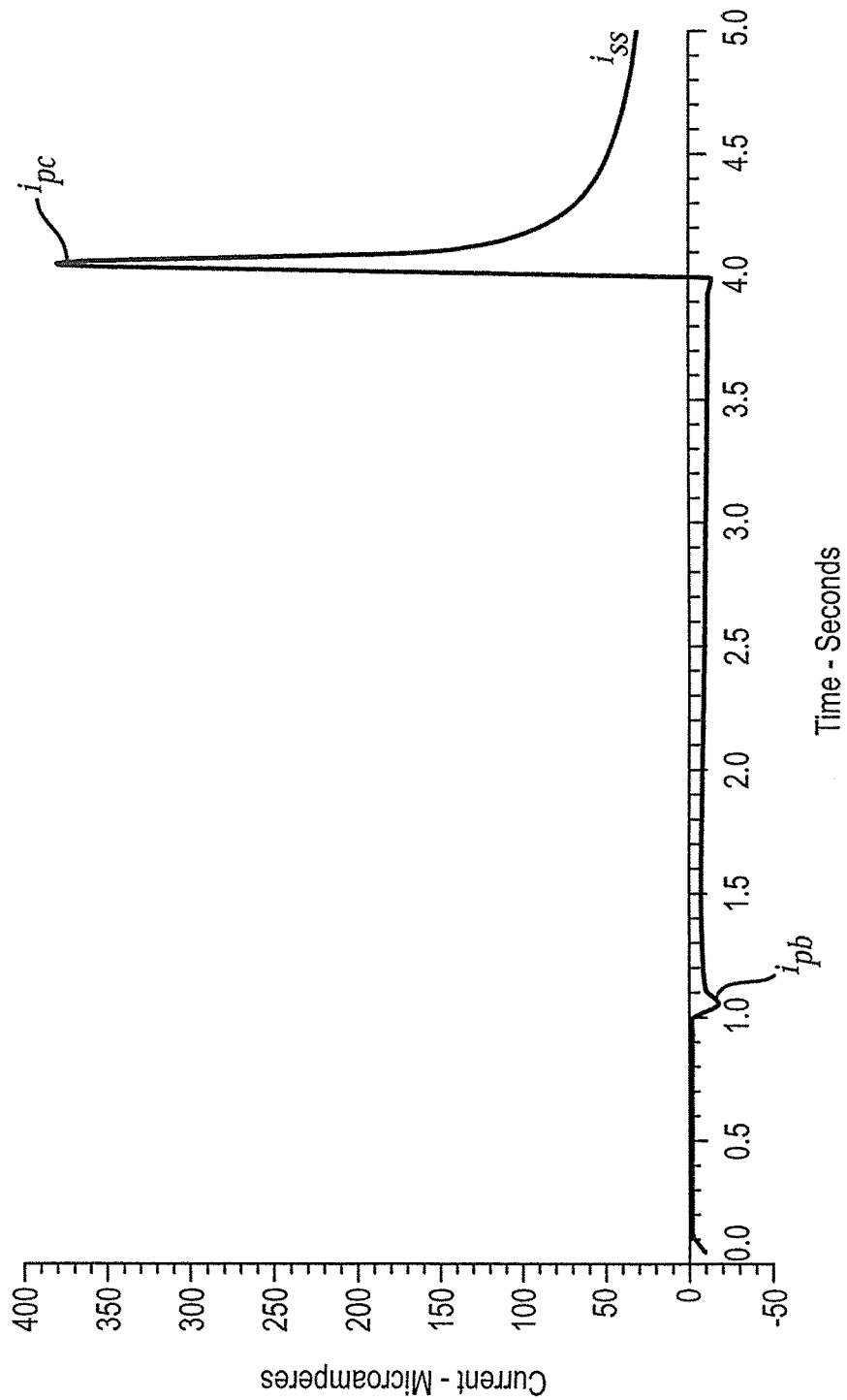
FIG. 7 shows a test current transient generated with the test voltage waveform of FIG. 6.

The first time interval $t_1$ may be sufficiently long so that the sample-receiving chamber 61 can fully fill with sample and also so that the reagent layer 72 can at least partially dissolve or solvate. In one aspect, the first test voltage $V_1$ may be a value relatively close to the redox potential of the mediator so that a relatively small amount of a reduction or oxidation current is measured. FIG. 7 shows that a relatively small amount of current is observed during the first time interval $t_1$ compared to the second and third time intervals $t_2$ and $t_3$. For example, when using ferricyanide and/or ferrocyanide as the mediator, the first test voltage $V_1$ can range from about −100 mV to about −1 mV, preferably range from about −50 mV to about −5 mV, and most preferably range from about −30 mV to about −10 mV.

After applying the first test voltage $V_1$, the test meter 100 applies a second test voltage $V_2$ between first electrode 166 and second electrode 164 (e.g., −0.3 Volts in FIG. 6), for a second time interval $t_2$ (e.g., about 3 seconds in FIG. 6). The second test voltage $V_2$ may be a value sufficiently negative of the mediator redox potential so that a limiting oxidation current is measured at the second electrode 164. For example, when using ferricyanide and/or ferrocyanide as the mediator, the second test voltage $V_2$ can range from about −600 mV to about zero mV, preferably range from about −600 mV to about −100 mV, and more preferably be about −300 mV.

The second time interval $t_2$ should be sufficiently long so that the rate of generation of reduced mediator (e.g., ferrocyanide) can be monitored based on the magnitude of a limiting oxidation current. Reduced mediator is generated by enzymatic reactions with the reagent layer 72. During the second time interval $t_2$, a limiting amount of reduced mediator is oxidized at second electrode 164 and a non-limiting amount of oxidized mediator is reduced at first electrode 166 to form a concentration gradient between first electrode 166 and second electrode 164.

In an exemplary embodiment, the second time interval $t_2$ should also be sufficiently long so that a sufficient amount of ferricyanide can be generated at the second electrode 164. A sufficient amount of ferricyanide is required at the second electrode 164 so that a limiting current can be measured for oxidizing ferrocyanide at the first electrode 166 during the third test voltage $V_3$. The second time interval $t_2$ may be less than about 60 seconds, and preferably can range from about 1 second to about 10 seconds, and more preferably range from about 2 seconds to about 5 seconds. Likewise, the time interval indicated as $t_{cap}$ in FIG. 6 may also last over a range of times, but in one exemplary embodiment it has a duration of about 20 milliseconds. In one exemplary embodiment, the superimposed alternating test voltage component is applied after about 0.3 seconds to about 0.4 seconds after the application of the second test voltage $V_2$, and induces a sine wave having a frequency of about 109 Hz with an amplitude of about +/−50 mV.

FIG. 7 shows a relatively small peak $i_{pb}$ at the beginning of the second time interval $t_2$ followed by a gradual increase of an absolute value of an oxidation current during the second time interval $t_2$. The small peak $i_{pb}$ occurs due to an initial depletion of reduced mediator at about 1 second. The gradual absolute increase in oxidation current after the small peak $i_{pb}$ is caused by the generation of ferrocyanide by reagent layer 72, which then diffuses to second electrode 164.

After applying the second test voltage $V_2$, the test meter 100 applies a third test voltage $V_3$ between the first electrode 166 and the second electrode 164 (e.g., about +0.3 Volts in FIG. 6) for a third time interval $t_3$ (e.g., 1 second in FIG. 6). The third test voltage $V_3$ may be a value sufficiently positive of the mediator redox potential so that a limiting oxidation current is measured at the first electrode 166. For example, when using ferricyanide and/or ferrocyanide as the mediator, the third test voltage $V_3$ can range from about zero mV to about 600 mV, preferably range from about 100 mV to about 600 mV, and more preferably be about 300 mV.

The third time interval $t_3$ may be sufficiently long to monitor the diffusion of reduced mediator (e.g., ferrocyanide) near the first electrode 166 based on the magnitude of the oxidation current. During the third time interval $t_3$, a limiting amount of reduced mediator is oxidized at first electrode 166 and a non-limiting amount of oxidized mediator is reduced at the second electrode 164. The third time interval $t_3$ can range from about 0.1 seconds to about 5 seconds and preferably range from about 0.3 seconds to about 3 seconds, and more preferably range from about 0.5 seconds to about 2 seconds.

FIG. 7 shows a relatively large peak $i_{pc}$ at the beginning of the third time interval $t_3$ followed by a decrease to a steady-state current $i_{ss}$ value. In one embodiment, the second test voltage $V_2$ can have a first polarity and the third test voltage $V_3$ may have a second polarity that is opposite to the first polarity. In another embodiment, the second test voltage $V_2$ can be sufficiently negative of the mediator redox potential and the third test voltage $V_3$ can be sufficiently positive of the mediator redox potential. The third test voltage $V_3$ may be applied immediately after the second test voltage $V_2$. However, one skilled in the art will appreciate that the magnitude and polarity of the second and third test voltages can be chosen depending on the manner in which analyte concentration is determined.

Figure 8:
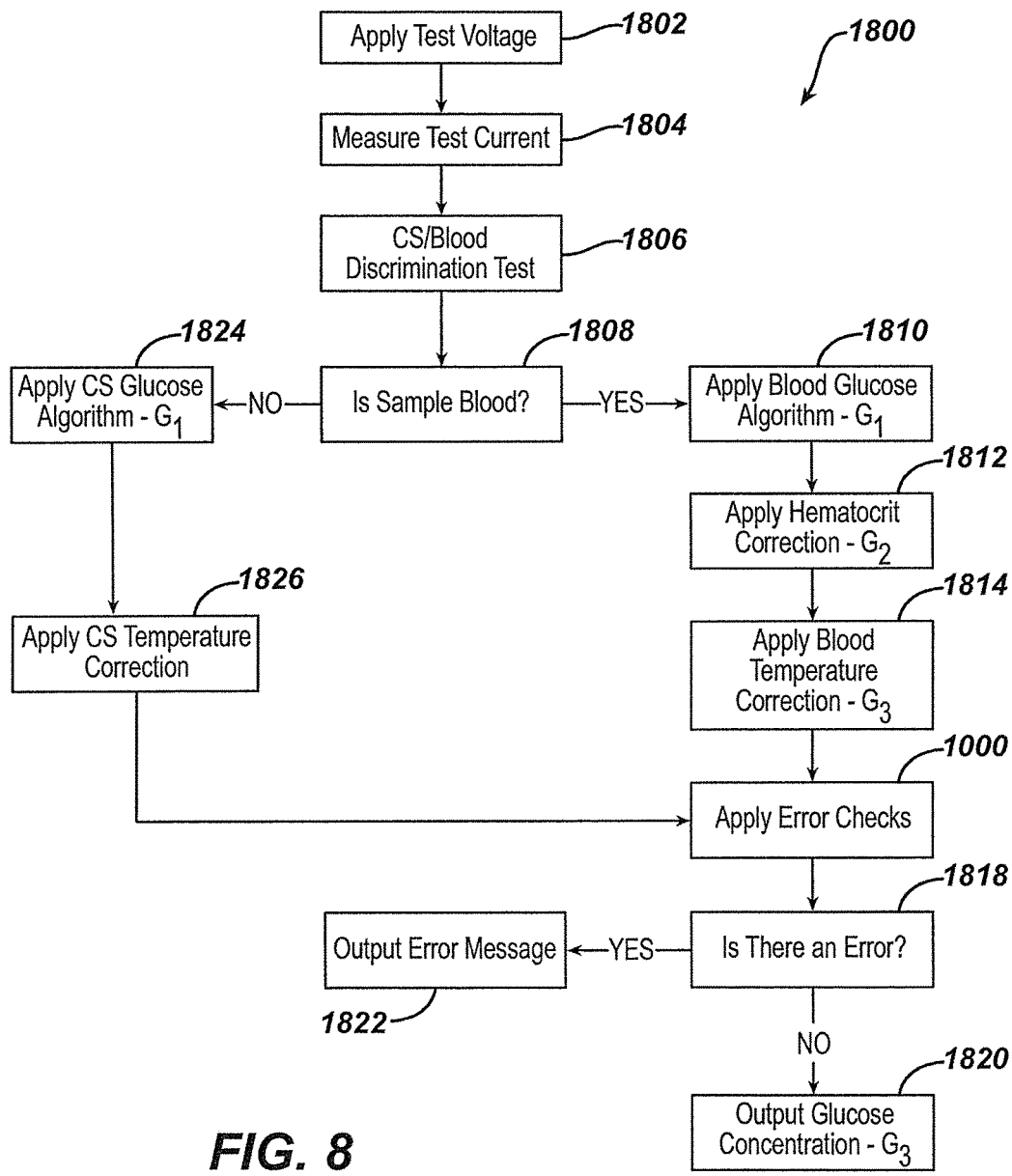
FIG. 8 is a flow diagram showing an embodiment of a method of determining a glucose concentration.

FIG. 8 illustrates one method of determining a glucose concentration by way of a flow diagram. A user can insert a test strip into a test meter and then apply a sample to the test strip. The test meter detects the presence of the sample and applies a test voltage, as shown in a step 1802. In response to the test voltage, the test meter measures a test current, as shown in a step 1804. A microprocessor of the test meter can then process the resulting test current values so that an accurate glucose measurement can be determined and to ensure that there are no system errors.

Another step in the method, as shown in step 1806, can be performing a control solution (CS)/blood discrimination test. As indicated in step 1808, if the CS/blood discrimination test determines that the sample is blood, then method 1800 moves to a series of steps that include: the application of a blood glucose algorithm 1810, hematocrit correction 1812, blood temperature correction 1814, and error checks 1000; and if the CS/blood discrimination test determines that the sample is CS (i.e., not blood), then method 1800 moves to a series of steps that include: the application of a CS glucose algorithm 1824, CS temperature correction 1826, and error checks 1000. After performing the error checks 1000, step 1818 can be performed to determine if there are any errors. If there are no errors, then the test meter outputs a glucose concentration, as shown in a step 1820, but if there are errors, then the test outputs an error message, as shown in a step 1822.

Control Solution (CS)/Blood Discrimination Test

The CS/blood discrimination test 1806 can include a first reference value and a second reference value. The first reference value can be based on current values during the first time interval $t_1$ and the second reference value can be based on current values during both the second time interval $t_2$ and the third time interval $t_3$. In one embodiment the first reference value can be obtained by performing a summation of the current values obtained during the first time current transient when using the test voltage waveform of FIG. 6. By way of non-limiting example, a first reference value $i_{sum}$ can be represented by Equation 1:

$$i_{sum} = \sum_{t=0.05}^{1} i(t) \qquad \text{Eq. 1}$$

where the term $i_{sum}$ is the summation of current values and t is a time. The second reference value, sometimes referred to as the residual reaction index, can be obtained by a seventh ratio $R_7$ of current values during the second time interval and the third time interval, as shown in Eq. 2:

$$R_7 = \text{abs}\left(\frac{i(3.8)}{i(4.15)}\right) \qquad \text{Eq. 2}$$

where abs represents an absolute function and 3.8 and 4.15 represent the time in seconds of the second and third time intervals, respectively, for this particular example. A discrimination criterion can be used to determine if the sample is either control solution or blood based on the first reference value of Eq. 1 and the second reference of Eq. 2. For example, the first reference value of Eq. 1 can be compared to a pre-determined threshold and the second reference value of Eq. 2 can be compared to a pre-determined threshold equation. The predetermined threshold may be about 12 microamperes. The pre-determined threshold equation can be based on a function using the first reference value of Eq. 1. More specifically, as illustrated by Eq. 3, the pre-determined threshold equation can be:

$$\frac{z_1 * (i_{sum} - 12)}{i_{sum}} \qquad \text{Eq. 3}$$

where $Z_1$ can be a constant such as, for example, about 0.2. Thus, the CS/Blood discrimination test 1806 can identify a sample as blood if $$i_{sum} > 12 \text{ and if } R_7 < \frac{z_1 * (i_{sum} - 12)}{i_{sum}}$$

else the sample is a control solution.

Blood Glucose Algorithm

If the sample is identified as a blood sample, the blood glucose algorithm of step 1810 can be performed on the test current values. A first glucose concentration $G_1$ can be calculated using a glucose algorithm as shown in Equation 4:

$$G_1 = \left(\frac{i_2}{i_3}\right)^p \times (ax i_1 - z) \qquad \text{Eq. 4}$$

where $i_1$ is a first test current value, $i_2$ is a second test current value, $i_3$ is a third test current value, and the terms a, p, and z can be empirically derived calibration constants. All test current values (e.g., $i_1$, $i_2$, and $i_3$) in Equation 4 use the absolute value of the current. The first test current value $i_1$ and the second test current value $i_2$ can each be defined by an average or summation of one or more predetermined test current values that occur during the third time interval $t_3$. The third test current value $i_3$ can be defined by an average or summation of one or more predetermined test current values that occur during the second time interval $t_2$. One skilled in the art will appreciate that names "first" "second," and "third" are chosen for convenience and do not necessarily reflect the order in which the current values are calculated.

Equation 4 can be modified to provide an even more accurate glucose concentration. Instead of using a simple average of summation of test current values, the term $i_1$ can be defined to include peak current values $i_{pb}$ and $i_{pc}$ and the steady-state current $i_{ss}$, as shown in Equation 5:

$$i_1 = i_2 \left\{ \frac{i_{pc} - 2i_{pb} + i_{ss}}{i_{pc} + i_{ss}} \right\} \qquad \text{Eq. 5}$$

where a calculation of the steady-state current $i_{ss}$ can be based on a mathematical model, an extrapolation, an average at a predetermined time interval, a combination thereof, or any number of other ways for calculating a steady-state current. Some examples of methods for calculating $i_{ss}$ can be found in U.S. Pat. Nos. 5,942,102 and 6,413,410, each of which is hereby incorporated by reference in its entirety.

Alternatively, $i_{ss}$ may be estimated by multiplying the test current value at 5 seconds with a constant $K_8$ (e.g., 0.678). Thus, $i_{ss} \cong i(5) \times K_8$. The term $K_8$ can be estimated using Equation 6:

$$i_{ss} = \frac{i(5)}{1 + 4\exp\left(\frac{-4\pi^2 D x 0.975}{L^2}\right)} \qquad \text{Eq. 6}$$

where the number 0.975 is about the time in seconds after the third test voltage $V_3$ is applied that corresponds to i(5), which, assuming a linear variation over the time between about 0.95 seconds and 1 second, is the average current between 0.95 and 1 second, the term D is assumed to be about $5 \times 10^{-6}$ cm$^2$/sec as a typical diffusion coefficient in blood, and the term L is assumed to be about 0.0095 cm, which represents the height of the spacer 60.

Turning again to Eq. 5, $i_{pc}$ may be the test current value at 4.1 seconds, and $i_{pb}$ may be the test current value at 1.1 seconds, based on the test voltage and test current waveforms in FIGS. 6 and 7.

Turning back to Eq. 4, $i_2$ can be defined to be $$i_2 = \sum_{t=4.4}^{5} i(t)$$

and $i_3$ can be defined to be $$i_3 = \sum_{t=1.4}^{4} i(t).$$

Equation 5 can be combined with Equation 4 to yield an equation for determining a more accurate glucose concentration that can compensate for the presence of endogenous and/or exogenous interferents in a blood sample, as shown in Equation 7:

$$G_1 = \left(\frac{i_2}{i_3}\right)^p \times \left(a \times i_2 \times \left\{\frac{i_{pc} - 2i_{pb} + i_{ss}}{i_{pc} + i_{ss}}\right\} - z\right) \qquad \text{Eq. 7}$$

where the first glucose concentration $G_1$ is the output of the blood glucose algorithm and the terms a, p, and z are constants that can be derived empirically.

CS Glucose Algorithm

If the sample is identified as a CS, the CS glucose algorithm of step 1824 can be performed on the test current values. A first glucose concentration $G_1$ for CS can be calculated using Equation 7 above, although the values for a, p, and z for CS can be different than those for blood.

Analyte Detection at Extreme Hematocrit Levels:

In addition to endogenous interferents, extreme hematocrit levels under certain circumstances can affect the accuracy of a glucose measurement. Thus, hematocrit correction 1812 can be applied by modifying $G_1$ to provide a second glucose concentration $G_2$ that is accurate even if the sample has an extreme hematocrit level (e.g., about 20% or about 60%).

Figure 9:
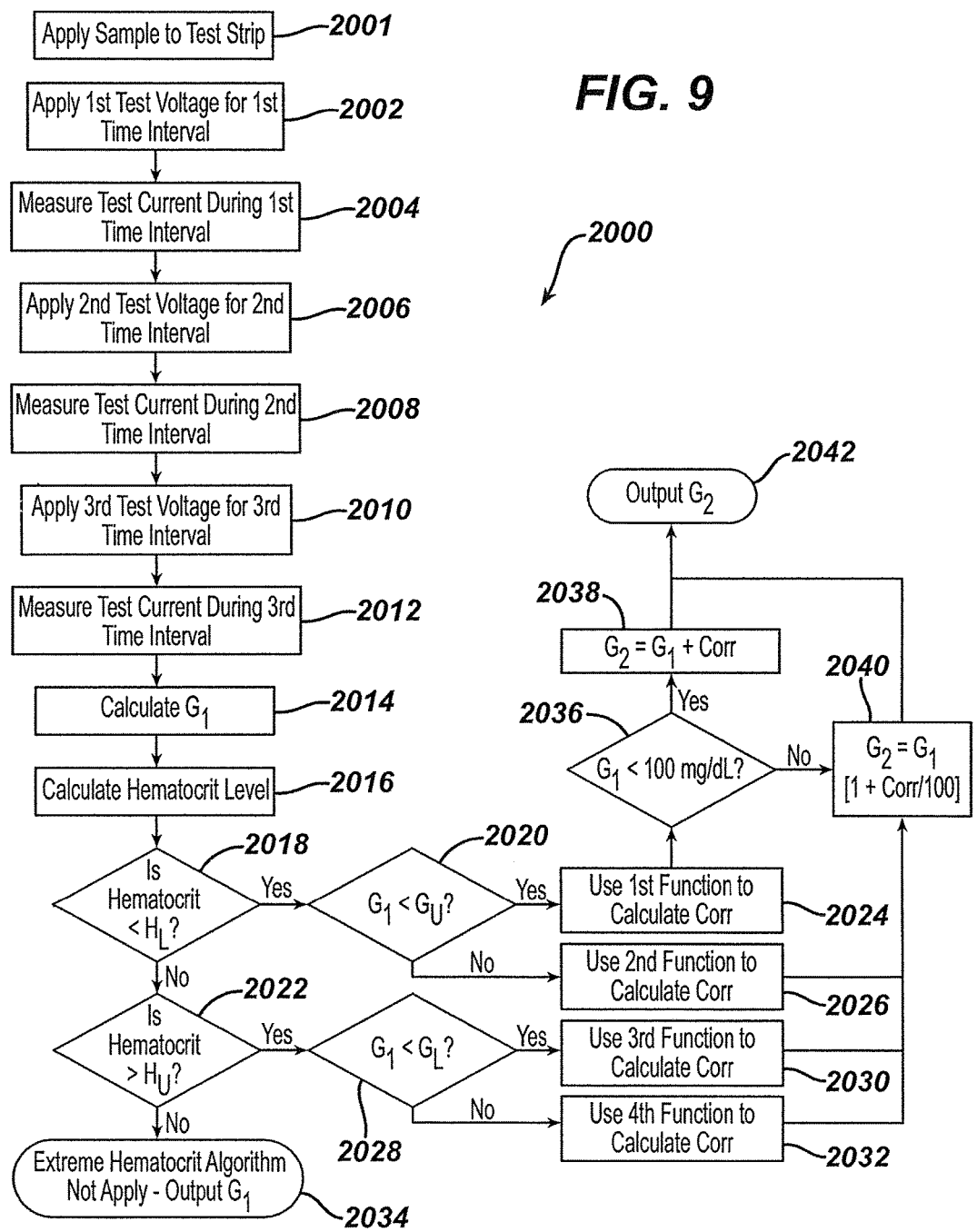
FIG. 9 is a flow diagram showing an exemplary embodiment of a blood glucose algorithm and a hematocrit correction.

Methods and systems of accurately measuring glucose concentrations in extreme hematocrit samples are provided herein. For example, FIG. 9 is a flow diagram depicting a method 2000 for calculating an accurate glucose concentration that accounts for blood samples having an extreme hematocrit level. A user can initiate a test by applying a sample to the test strip, as shown in a step 2001. A first test voltage $V_1$ can be applied for a first time interval $t_1$ as shown in a step 2002. The resulting test current is then measured for the first time interval $t_1$, as shown in a step 2004. After the first time interval $t_1$, the second test voltage $V_2$ is applied for a second time interval $t_2$, as shown in a step 2006. The resulting test current is then measured for the second time interval $t_2$, as shown in a step 2008. After the second time interval $t_2$, the third test voltage $V_3$ is applied for a third time interval $t_3$, as shown in a step 2010. The resulting test current is then measured for the third time interval $t_3$, as shown in a step 2012.

Now that test current values have been collected by a test meter, a first glucose concentration $G_1$ can be calculated, as shown in a step 2014. The first glucose concentration $G_1$ can be calculated using Equations 4 or 7. Next, a hematocrit level H can be calculated, as shown in a step 2016.

Figure 10:
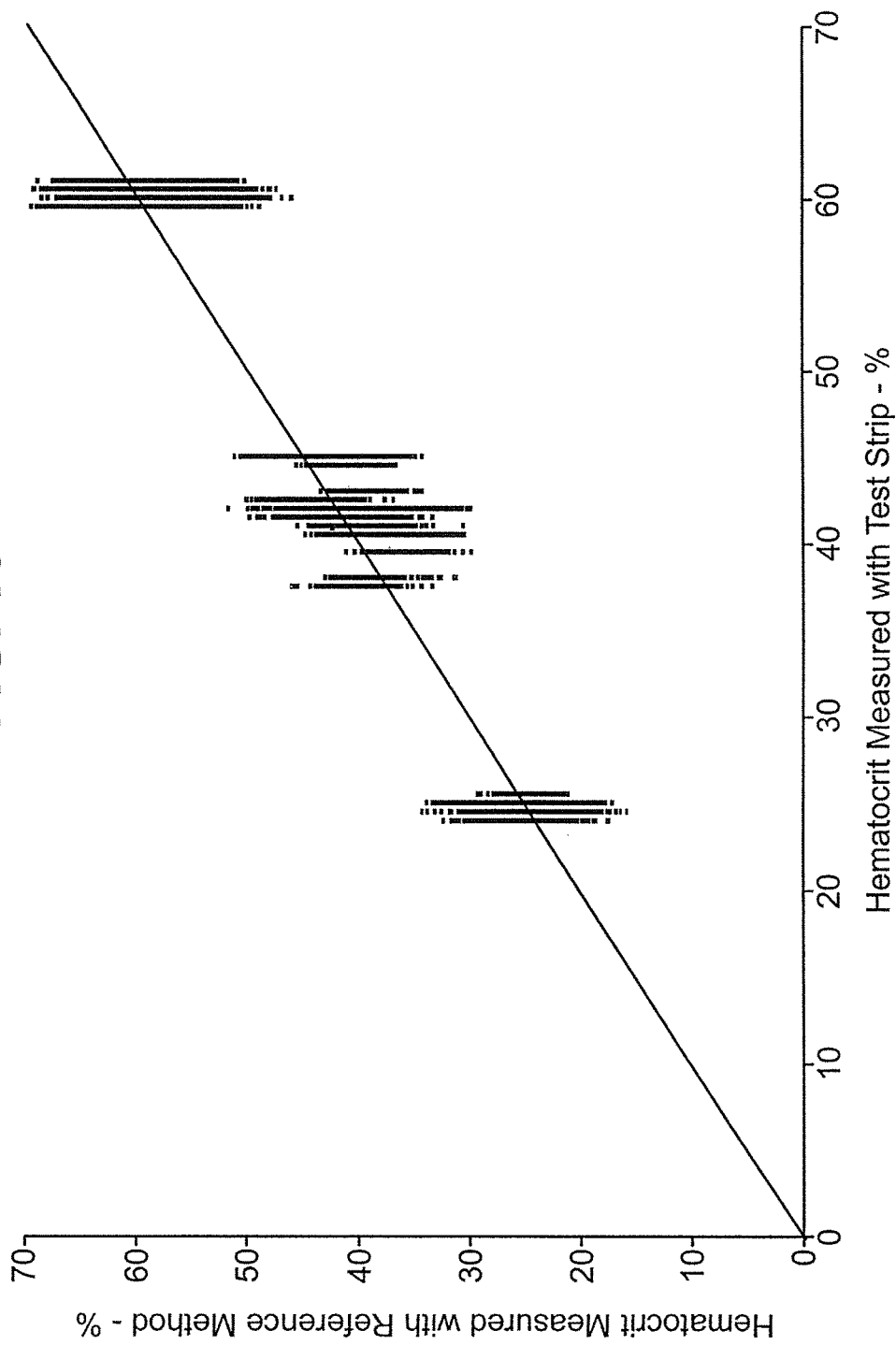
FIG. 10 is a chart showing a correlation between measured hematocrit levels using a reference method and measured hematocrit levels using the test strip of FIG. 1.

The hematocrit level may be estimated using test current values acquired during the glucose test time interval $t_G$. Alternatively, the hematocrit level H may be estimated using test current values acquired during the second time interval $t_2$ and the third time interval $t_3$. In one embodiment, the hematocrit level H can be estimated using a hematocrit equation based upon the first glucose concentration $G_1$ and $i_2$. An exemplary hematocrit equation is shown in Equation 8:

$$H = K_5 \ln(|i_2|) + K_6 \ln(G_1) + K_7 \qquad \text{Eq. 8}$$

where H is the hematocrit level, $i_2$ is at least one current value during the second time interval, $K_5$ is a fifth constant, $K_6$ is a sixth constant, and $K_7$ is a seventh constant. When GDH-PQQ is the enzyme, $K_5$, $K_6$, and $K_7$ may be about −76, 56, and 250, respectively. When FAD-GDH is the enzyme, $K_5$, $K_6$, and $K_7$ may be about −73.5, 58.8, and 213, respectively. FIG. 10 shows that the estimated hematocrit levels using Equation 8 has an approximately linear correlation with actual hematocrit levels measured with a reference method.

Once the hematocrit level H has been calculated in step 2016, it is compared to a lower predetermined hematocrit level $H_L$, as shown in a step 2018. The lower predetermined hematocrit level $H_L$ may be about 30%. If the hematocrit level H is less than lower predetermined hematocrit level $H_L$, then the first glucose concentration $G_1$ is compared to an upper predetermined glucose concentration $G_u$, as shown in a step 2020. The upper predetermined glucose concentration $G_u$ may be about 300 mg/dL. If the hematocrit level H is compared to an upper predetermined hematocrit level $H_u$, as shown in a step 2022. The upper predetermined hematocrit level $H_u$ may be about 50%. If the hematocrit level H is greater than $H_u$, then the first glucose concentration $G_1$ is compared to a lower predetermined glucose concentration $G_L$, as shown in a step 2028. The lower predetermined glucose concentration $G_L$ may be about 100 mg/dL. Steps 2018 and 2022 indicate that method 2000 will output first glucose concentration $G_1$, as shown in a step 2034, if the hematocrit level H is not less than $H_L$ and not greater than $H_u$.

A first function can be used to calculate a correction value Corr, as shown in a step 2024, if the first glucose concentration $G_1$ is less than the upper predetermined glucose concentration $G_u$. The first function may be in the form of Equation 9:

$$\text{Corr} = K_1(H_L - H)G_1 \qquad \text{Eq. 9}$$

where $K_1$ is a first constant and $H_L$ is the lower predetermined hematocrit level. In one embodiment $K_1$ and $H_L$ may be about −0.004 and about 30%, respectively.

However, if the first glucose concentration $G_1$ is not less than the upper predetermined glucose concentration $G_u$, then the second function can be used to calculate the correction value Corr, as shown in a step 2026. The second function may be in the form of Equation 10:

$$\text{Corr} = K_2(H_L - H)(G_{max} - G_1) \qquad \text{Eq. 10}$$

where $K_2$ is a second constant and $G_{max}$ is a predetermined maximum glucose concentration. In one embodiment $K_2$ and $G_{max}$ may be about −0.004 and about 600 mg/dL, respectively. The correction value Corr for Equations 9 and 10 may be restricted to a range of about −5 to about zero. Thus, if Corr is less than −5, then Corr is set to −5 and if Corr is greater than zero, then Corr is set to zero.

A third function can be used to calculate a correction value Corr, as shown in a step 2030, if the first glucose concentration $G_1$ is less than lower predetermined glucose concentration $G_L$. The third function may be in the form of Equation 11:

$$\text{Corr} = 0 \qquad \text{Eq. 11}$$

however, if the first glucose concentration $G_1$ is not less than the lower predetermined glucose concentration $G_L$, then the fourth function can be used to calculate the correction value Corr, as shown in a step 2032. The fourth function may be in the form of Equation 12:

$$\text{Corr} = K_4(H - H_U)(G_1 - G_L) \qquad \text{Eq. 12}$$

where $K_4$ is a fourth constant, which may be about 0.011. The correction value Corr for Equation 12 may be restricted to a range of about zero to about six. Thus, if Corr is less than zero, then Corr is set to zero and if Corr is greater than six, then Corr is set to six.

After calculating Corr with the first function in step 2024, the first glucose concentration is compared to 100 mg/dL in a step 2036. If the first glucose concentration is less than 100 mg/dL, then the second glucose concentration $G_2$ is calculated using a first correction equation, as shown in a step 2038. Note that the 100 mg/dL represents a glucose threshold and should not be construed as a limiting number. In one embodiment, the glucose threshold may range from about 70 mg/dL to about 100 mg/dL. The first correction equation may be in the form of Equation 13:

$$G_2 = G_1 + \text{Corr} \qquad \text{Eq. 13}$$

If the first glucose concentration $G_1$ is not less than 100 mg/dL based on step 2036, then the second glucose concentration $G_2$ is calculated using a second correction equation, as shown in a step 2040. The second correction equation may be in the form of Equation 14:

$$G_2 = G_1\left(1 + \frac{\text{Corr}}{100}\right) \qquad \text{Eq. 14}$$

After the second glucose concentration $G_2$ is calculated in either steps 2038 or 2040, it is outputted as a glucose reading in a step 2042.

After calculating Corr in step 2026, 2030, or 2032, the second glucose concentration $G_2$ can be calculated using Equation 14, as shown in step 2040. When Corr equals zero (as for the third function), the second glucose concentration $G_2$ equals the first glucose concentration $G_1$, which can then be outputted as a glucose reading in step 2042.

Figure 11:
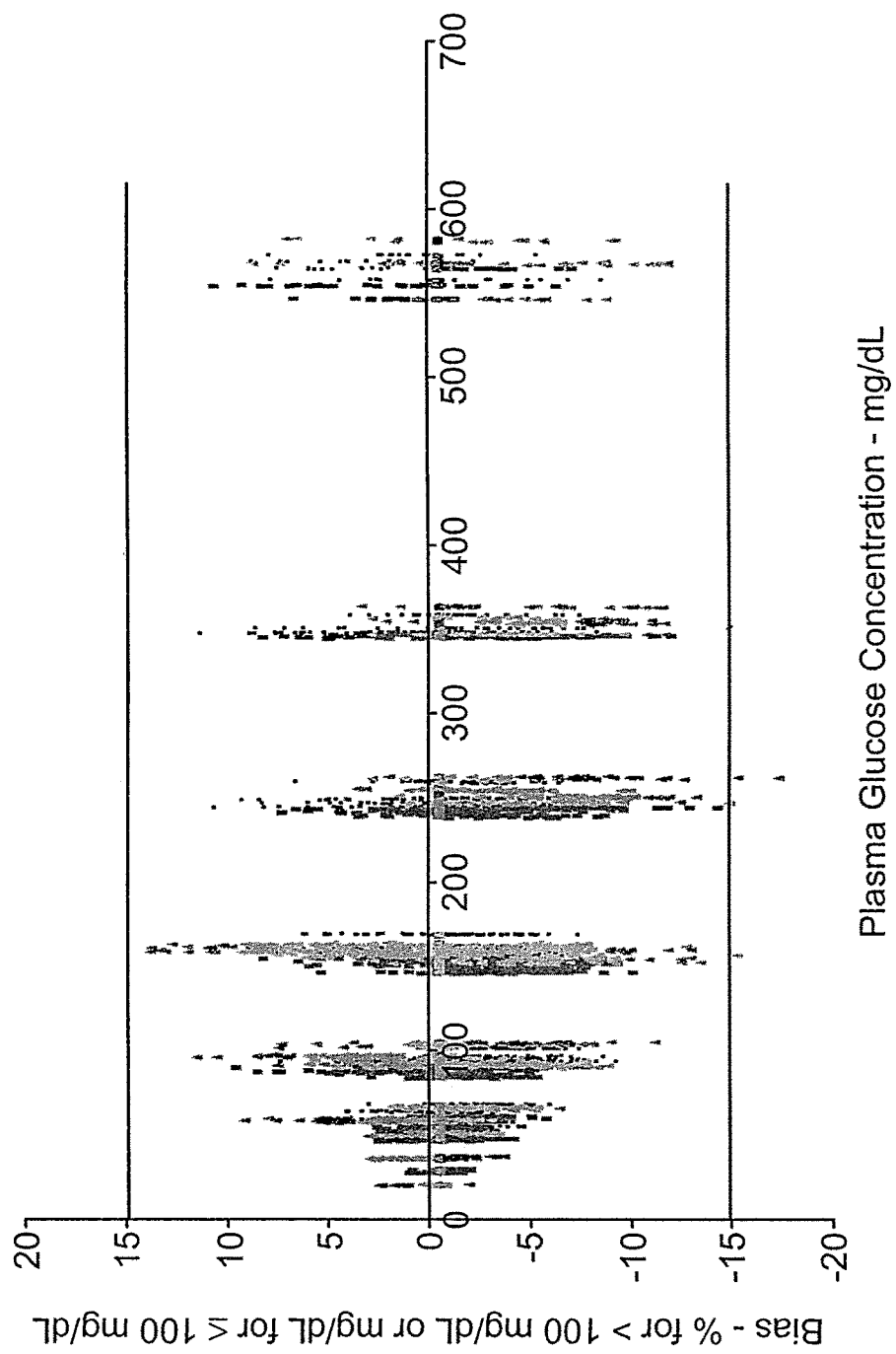
FIG. 11 is a bias plot showing a plurality of test strips that were tested with blood samples having a wide range of hematocrit levels.

The method 2000 for calculating accurate glucose concentrations in blood samples having extreme hematocrit levels was verified using blood from several donors. FIG. 11 shows a bias plot for a plurality of test strips that were tested with blood samples having a wide range of hematocrit levels and glucose concentrations. More specifically, FIG. 11 shows the effect of whole blood samples having a wide range of hematocrit on the accuracy and precision of the new test system. As shown, the bias of the sensor response with respect to the YSI 2700 (Yellow Springs Instruments, Yellow Springs, Ohio) is plotted against the plasma glucose concentration. The data were obtained with 3 batches of sensors and 4 blood donors. The hematocrit was adjusted to 20% (squares), 37-45% (circles) or 60% (triangles) prior to spiking the samples with glucose. These data suggest that the thin layer cell and tri-pulse approach for electrochemical measurement offers the opportunity for improved analytical performance with blood glucose test systems. Thus, the use of the correction value Corr, which depends on the hematocrit level H and the first glucose concentration $G_1$, allows for the determination of a more accurate second glucose concentration $G_2$ even if the blood sample has an extreme hematocrit level.

Blood Temperature Correction:

Turning back to FIG. 8, blood temperature correction 1814 can be applied to the test current values to provide a glucose concentration with an improved accuracy because of a reduced effect from temperature. A method for calculating a temperature corrected glucose concentration can include measuring a temperature value and calculating a second correction value $Corr_2$. The second correction value $Corr_2$ can be based on a temperature value and either first glucose concentration $G_1$ or second glucose concentration $G_2$ glucose concentration, both of which as described previously do not include a correction for temperature. Accordingly, the second correction value $Corr_2$ can then be used to correct the glucose concentration $G_1$ or $G_2$ for temperature.

Figure 12:
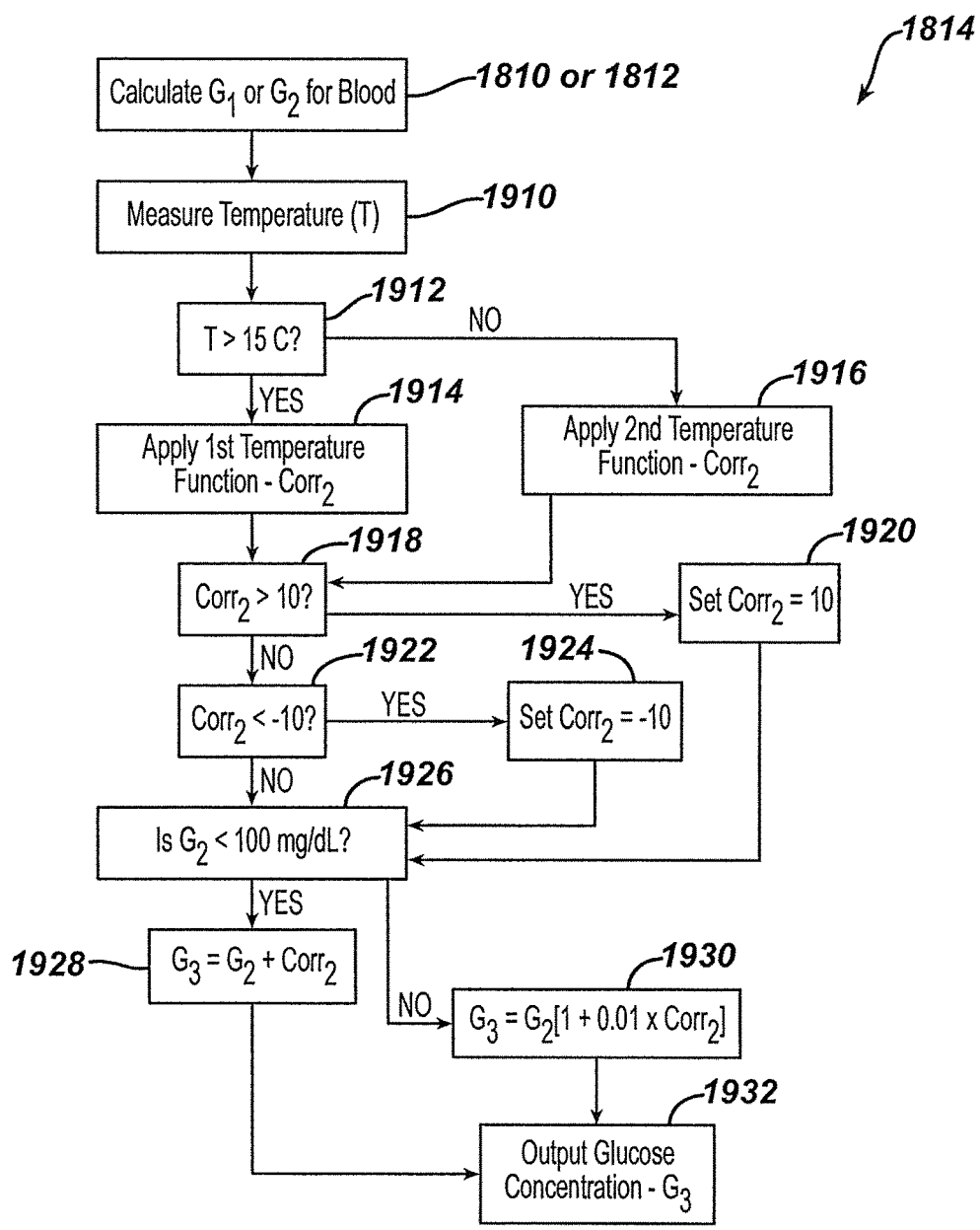
FIG. 12 is a flow diagram showing an embodiment of a method of applying a temperature correction when a sample is blood.

FIG. 12 is a flow diagram depicting an embodiment of the method 1814 of applying a blood temperature correction. Initially, a glucose concentration uncorrected for temperature can be obtained such as first glucose concentration $G_1$ from step 1810 or a second glucose concentration $G_2$ from step 1812. While a blood temperature correction can be applied to either $G_1$ or $G_2$, for simplicity the blood temperature correction will be described using $G_2$.

As shown in a step 1910 of the method 1814, a temperature value can be measured. The temperature can be measured using a thermistor or other temperature reading device that is incorporated into a test meter, or by way of any number of other mechanisms or means. Subsequently, a determination can be performed to determine whether the temperature value T is greater than a first temperature threshold $T_1$. As illustrated in FIG. 12, the temperature threshold $T_1$ is about 15° C. If the temperature value T is greater than 15° C., then a first temperature function can be applied to determine the second correction value $Corr_2$, as shown in a step 1914. If the temperature value T is not greater than 15° C., then a second temperature function can be applied to determine the second correction value $Corr_2$, as shown in a step 1916.

The first temperature function for calculating the second correction value $Corr_2$ can be in the form of Equation 15:

$$Corr_2 = -K_9(T-T_{RT}) + K_{10} \times G_2(T-T_{RT}) \qquad \text{Eq. 15}$$

where $Corr_2$ is the correction value, $K_9$ is a ninth constant (e.g., 0.57 for GDH-PQQ and 0.89 for FAD-GDH), T is a temperature value, $T_{RT}$ is a room temperature value (e.g., 22° C.), $K_{10}$ is a tenth constant (e.g., 0.00023 for GDH-PQQ and 0.00077 for FAD-GDH), and $G_2$ is the second glucose concentration. When T is about equal to $T_{RT}$, $Corr_2$ is about zero. In some instances, the first temperature function can be configured to have essentially no correction at room temperature such that variation can be reduced under routine ambient conditions. The second temperature function for calculating the second correction value $Corr_2$ can be in the form of Equation 16:

$$Corr_2 = -K_{11}(T-T_{RT}) + K_{12} \times G_2(T-T_{RT}) - K_{13} \times G_2(T-T_1) + K_{14} \times G_2(T-T_1) \qquad \text{Eq. 16}$$

where $Corr_2$ is the correction value, $K_{11}$ is an eleventh constant (e.g., 0.57 for GDH-PQQ and 0.89 for FAD-GDH), T is a temperature value, $T_{RT}$ is a room temperature value, $K_{12}$ is a twelfth constant (e.g., 0.00023 for GDH-PQQ and 0.00077 for FAD-GDH), G1 is a first glucose concentration, $K_{13}$ is a thirteenth constant (e.g., 0.63 for GDH-PQQ and 1.65 for FADGDH), $T_1$ is a first temperature threshold, and $K_{14}$ is a fourteenth constant (e.g., 0.0038 for GDH-PQQ and 0.0029 for FAD-GDH).

After the $Corr_2$ is calculated using either step 1914 or 1916, a couple of truncation functions can be performed to ensure that $Corr_2$ is constrained to a pre-determined range, thereby mitigating the risk of an outlier. In one embodiment $Corr_2$ can be limited to have a range of −10 to +10 by using a step 1918 and/or a step 1922. In the step 1918, a determination can be performed to determine whether $Corr_2$ is greater than 10. If $Corr_2$ is greater than 10, the $Corr_2$ is set to 10, as shown in a step 1920. If $Corr_2$ is not greater than 10, then a determination is performed to determine whether $Corr_2$ is less than −10, as shown in a step 1922. $Corr_2$ can be set to −10 if $Corr_2$ is less than −10, as shown in a step 1924. If $Corr_2$ is a value already in between −10 and +10, then there generally is no need for truncation.

Once $Corr_2$ is determined, a temperature corrected glucose concentration can be calculated using either a step 1928 or a step 1930. In a step 1926, a determination can be performed to determine whether the glucose concentration uncorrected for temperature (e.g., $G_2$) is less than 100 mg/dL. If $G_2$ is less than 100 mg/dL, then an Equation 17 can be used to calculate the temperature corrected glucose concentration $G_3$ by adding the correction value $Corr_2$ to the second glucose concentration $G_2$:

$$G_3 = G_2 + Corr_2 \qquad \text{Eq. 17}$$

If $G_2$ is not less than 100 mg/dL, then an Equation 18 can be used to calculate the temperature corrected glucose concentration $G_3$ by dividing $Corr_2$ by one hundred, adding one; and then multiplying by the second glucose concentration $G_2$:

$$G_3 = G_2[1 + 0.01 \times Corr_2] \qquad \text{Eq. 18}$$

Once a third glucose concentration is determined that has been corrected for the effects of temperature, the third glucose concentration can be outputted, as shown in a step 1932.

Figure 13:
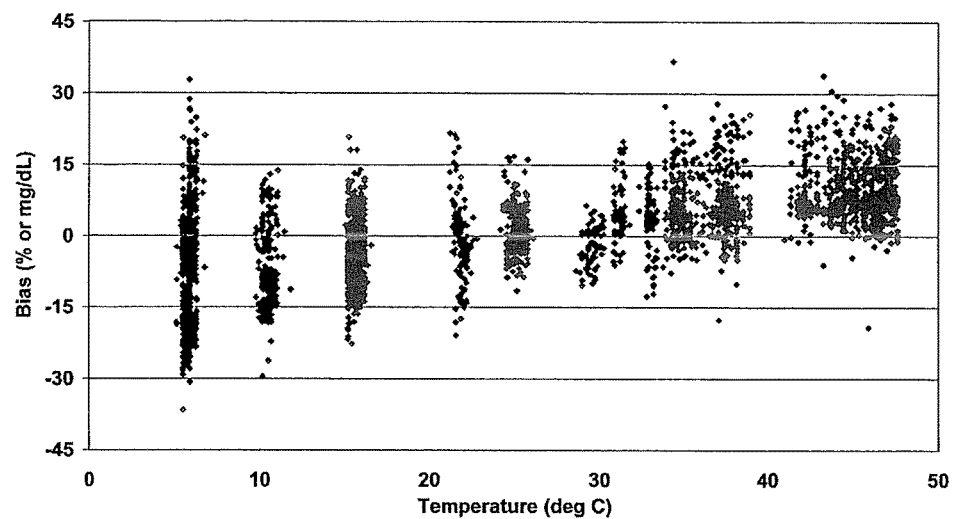
FIG. 13 is a bias plot showing a plurality of test strips that were tested with blood samples having a wide range of hematocrit levels, a wide range of glucose levels, and a wide range of temperature levels without temperature correction.
Figure 14:
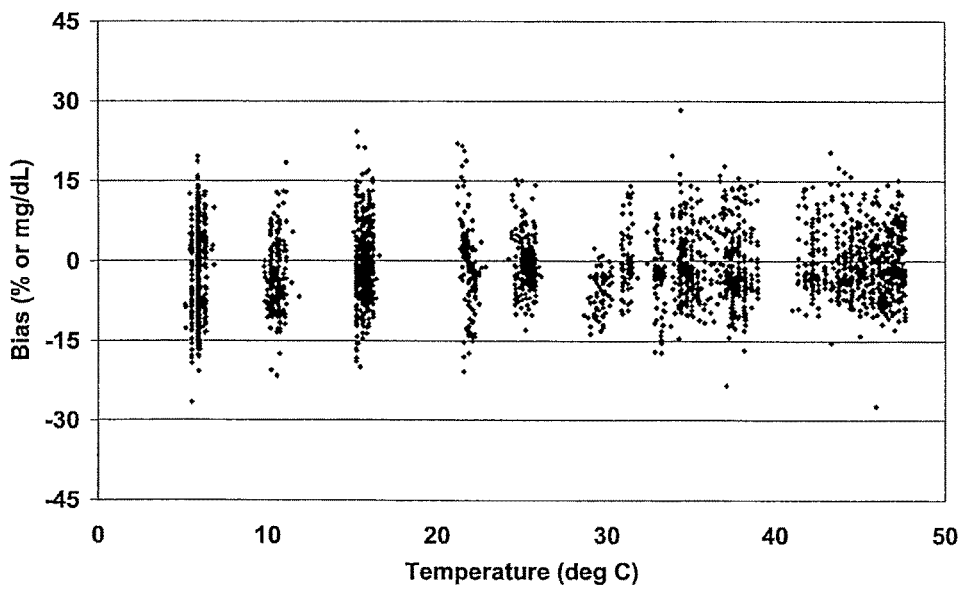
FIG. 14 is a bias plot showing a plurality of test strips that were tested with blood samples having a wide range of hematocrit levels, a wide range of glucose levels, and a wide range of temperature levels with temperature correction.

The method 1814 for blood temperature correction was verified using blood in a glove box over a temperature range of about 5° C. to 45° C. The blood samples had a hematocrit range of about 20-50% hematocrit and a glucose range of about 20-600 mg/dL equivalent plasma glucose concentration. The glove box was an enclosed chamber that could hold a pre-determined constant temperature. The glove portion of the glove box allowed a tester outside of the glove box to perform a glucose test inside the glove box. The tester inserted test strips into a test meter and dose sampled in an environment having both a controlled temperature and relative humidity (RH). The RH was maintained at about 60% in order to keep evaporation of the sample droplets at a relatively low level during the test. Generally the RH should not be too high to prevent condensation from occurring on the test meter. The blood was equilibrated to 37° C. outside the glove box, pipetted onto parafilm, rapidly moved into the glove box, and applied to the strips. This particular method allowed for the simulation of dosing capillary blood off a finger. FIG. 13 shows that temperature has a substantial bias on the blood results when there is no temperature compensation function in the test meters because only about 83.4% of biases were within 15% or 15 mg/dL of the reference glucose value. In contrast, as seen in FIG. 14, there is much less bias on the blood results when there is a temperature compensation in the test meters because far less biases percentage-wise were located outside of the 15% or 15 mg/dL range of the reference glucose value when compared to the results of FIG. 13.

Figure 15:
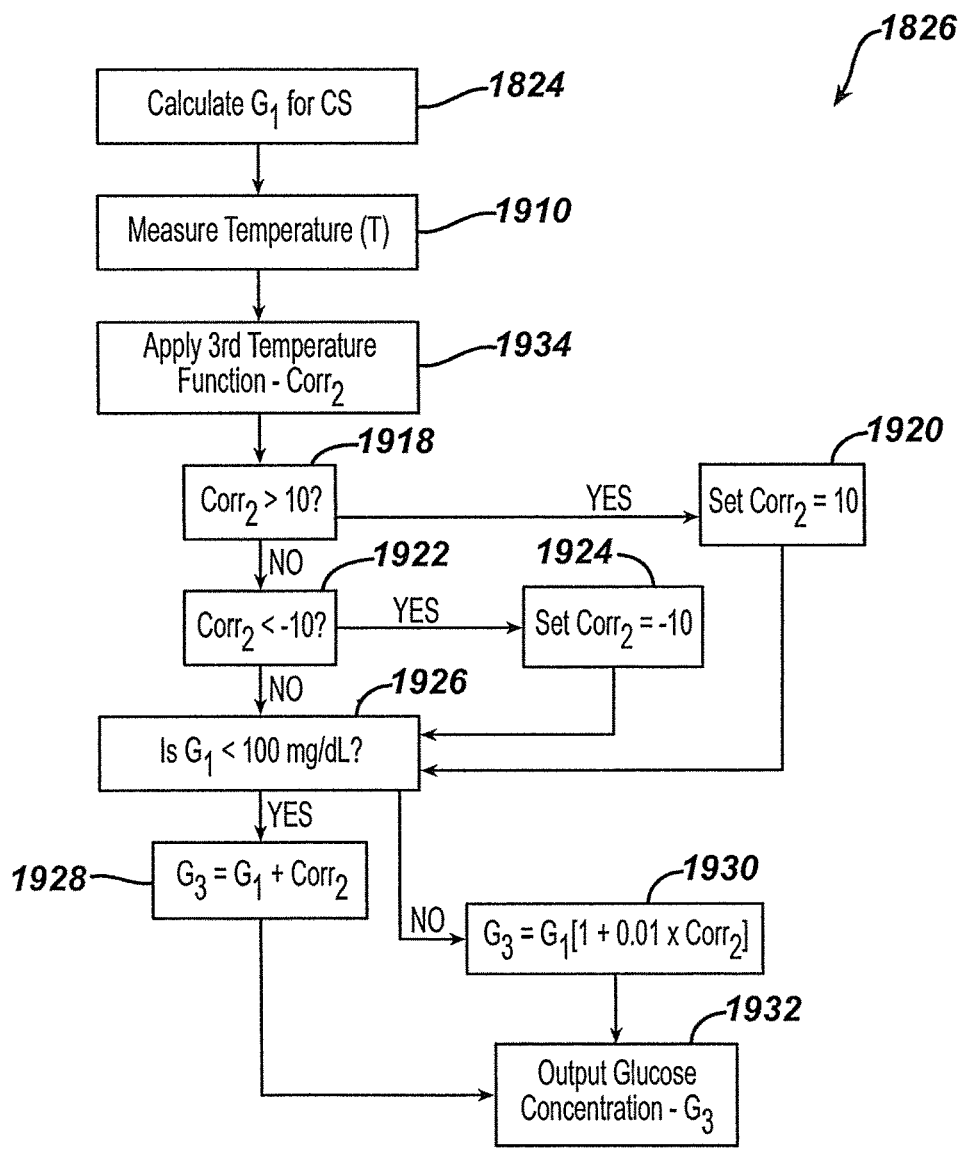
FIG. 15 is a flow diagram showing an embodiment of a method of applying a temperature correction when a sample is control solution.

Control Solution Temperature Correction:

FIG. 15 is a flow diagram depicting an embodiment of the method 1826 of applying a CS temperature correction. The CS temperature correction is similar to the blood temperature correction except that the temperature function for calculating $Corr_2$ is different.

Initially, a glucose concentration uncorrected for temperature can be obtained such as first glucose concentration $G_1$ from step 1824. Next, a temperature value can be measured, as shown in a step 1910. A third temperature function can be applied to determine the second correction value $Corr_2$ for CS, as shown in a step 1934. The third temperature function for calculating the second correction value $Corr_2$ can be in the form of Equation 19:

$$Corr_2 = -K_{15}(T-T_{RT}) - K_{16} \times G_2(T_2 - T_{RT})$$

where $K_{15}$ is a fifteenth constant (e.g., 0.27 for GDH-PQQ and 0.275 for FAD-GDH), T is a temperature value, $T_{RT}$ is a room temperature value (e.g., 22° C.), $K_{16}$ is a sixteenth constant (e.g., 0.0011 for GDH-PQQ and 0.00014 for FAD-GDH), and $G_2$ is the second glucose concentration.

Figure 20:
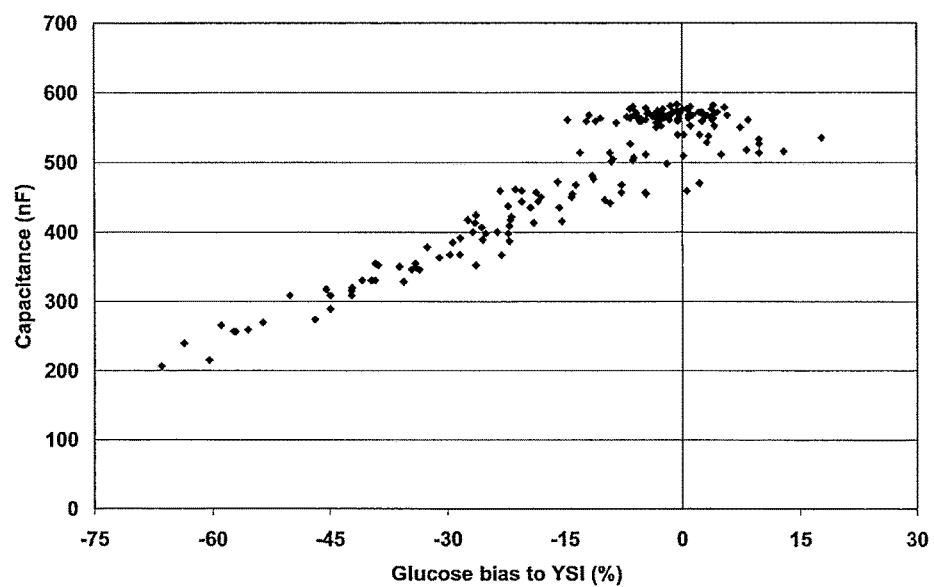
FIG. 20 is a chart showing a correlation of capacitance and bias to a reference glucose measurement (YSI, Yellow Springs Instrument) where capacitance values were measured for blood samples during the second test voltage of FIG. 6 (e.g., after approximately 1.3 seconds)

After the $Corr_2$ is calculated using step 1934, a couple of truncation functions can be performed to ensure that $Corr_2$ is constrained to a pre-determined range. In one embodiment $Corr_2$ can be limited to have a range of −10 to +10 by using a step 1918 and/or a step 1922, as shown in FIG. 20. In step 1918, a determination can be performed to determine whether $Corr_2$ is greater than 10. If $Corr_2$ is greater than 10, the $Corr_2$ can be set to 10, as shown in a step 1920. If $Corr_2$ is not greater than 10, then a determination can be performed to determine whether $Corr_2$ is less than −10, as shown in a step 1922. $Corr_2$ can be set to −10 if $Corr_2$ is less than −10, as shown in a step 1924.

Once $Corr_2$ is determined, a temperature corrected glucose concentration for CS can be calculated using either a step 1928 or a step 1930. In a step 1926, a determination can be performed to determine whether the glucose concentration uncorrected for temperature (e.g., $G_1$) is less than 100 mg/dL. If $G_1$ is less than 100 mg/dL, then third glucose concentration $G_3$ can be calculated by adding $G_1 + Corr_2$, as shown in step 1928. If $G_1$ is not less than 100 mg/dL, then third glucose concentration $G_3$ can be calculated by dividing $Corr_2$ by one hundred, adding one, and then multiplying by the second glucose concentration to give a temperature corrected concentration, as shown in step 1930. Once a third glucose concentration for CS is determined that is corrected for the effects of temperature, the third glucose concentration can be outputted, as shown in a step 1932, to either the next step in method 1800 or to error checks 1000.

Figure 16:
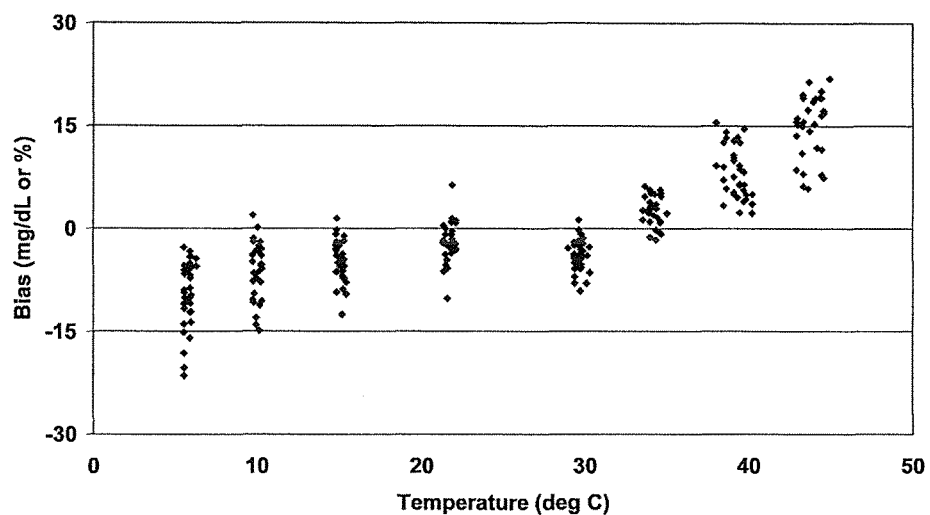
FIG. 16 is a bias plot showing a plurality of test strips that were tested with control solution samples having a wide range of glucose levels and a wide range of temperature levels without temperature correction.
Figure 17:
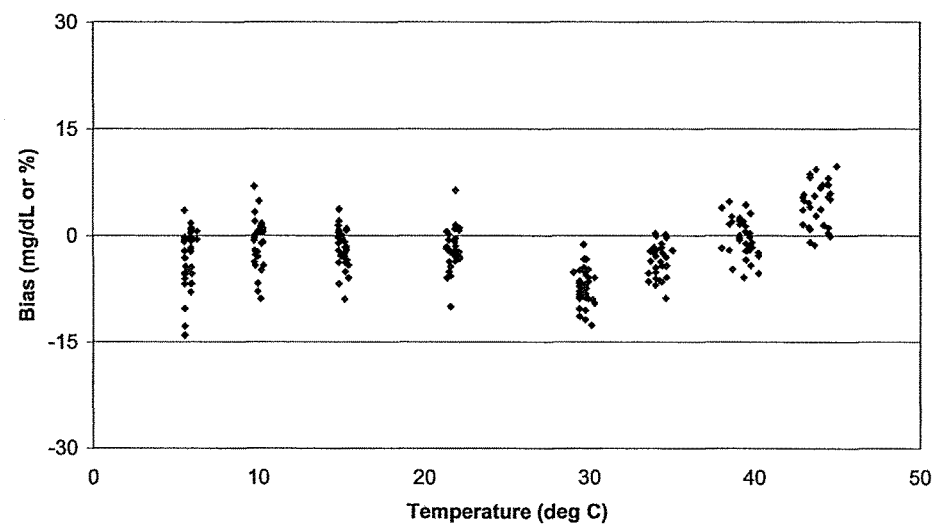
FIG. 17 is a bias plot showing a plurality of test strips that were tested with control solution samples having a wide range of glucose levels and a wide range of temperature levels with temperature correction.

The method 1826 for CS temperature correction was verified in a glove box over a temperature range of about 5° C. to 45° C. The relative humidity (RH) was maintained at about 60%. FIG. 16 shows that temperature has a substantial bias on the CS results when there is no temperature compensation function in the meters because a fair amount of the results fall outside of 15% or 15 mg/dL of the reference glucose value. In contrast, as seen in FIG. 17, there is much less bias on the blood results when there is a temperature compensation in the test meters because none of the results were located outside of the 15% or 15 mg/dL range of the glucose value.

Identifying System Errors:

Various embodiments of a method for identifying various system errors, which may include user errors when performing a test, test meter errors, and defective test strips, are also provided. The system can be configured to identify a test utilizing a partial fill or double-fill of a sample chamber. Also, the system can be configured to identify those situations where the sample may be leaking from the sample chamber thereby compromising the integrity of the testing and/or those situations where some portion of system (e.g., the test strip) is damaged.

Figure 18:
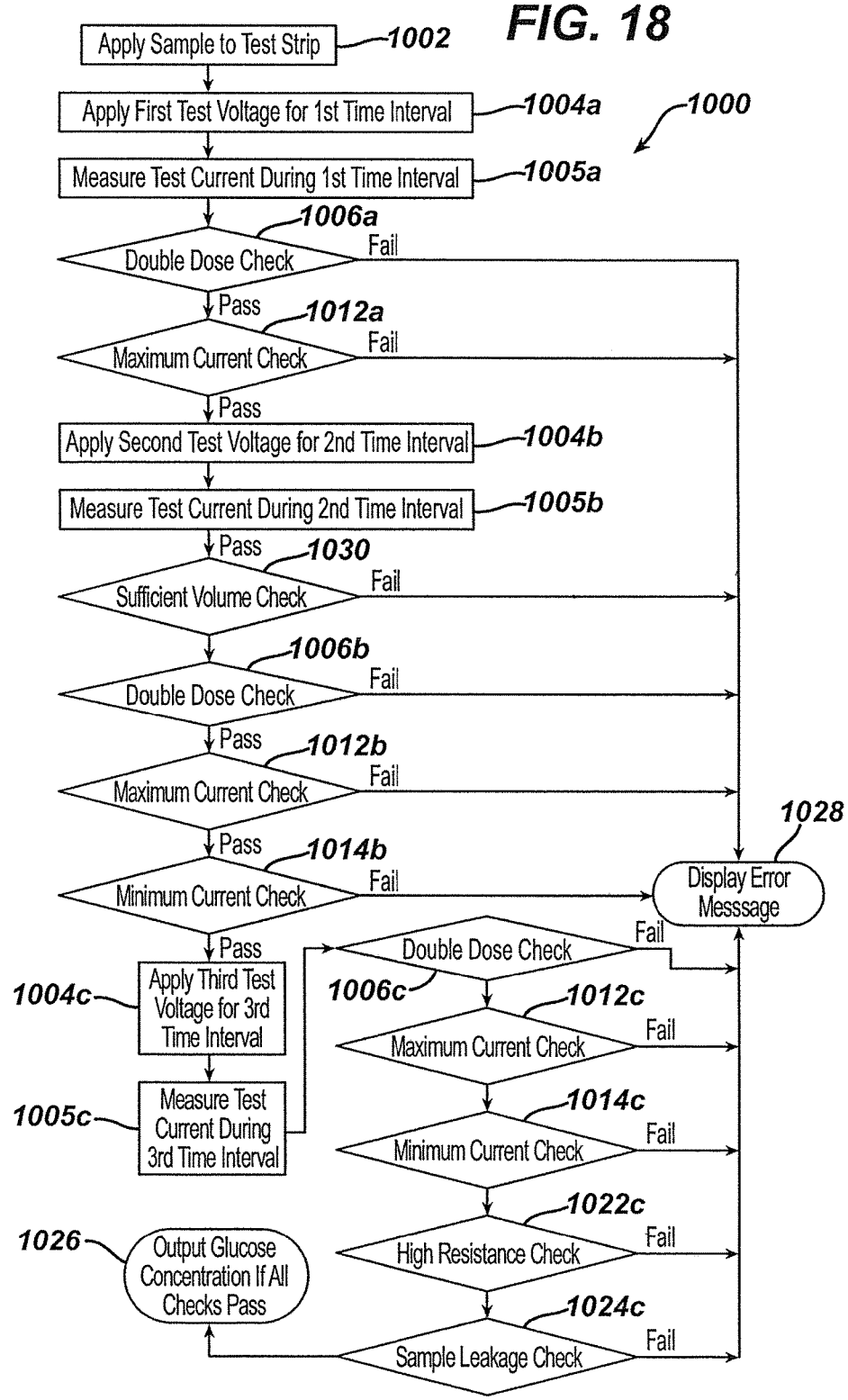
FIG. 18 is a flow diagram depicting an embodiment of a method of identifying system errors.

For example, FIG. 18 is a flow diagram depicting an exemplary embodiment of a method 1000 of identifying system errors in performing an analyte measurement. As shown, a user can initiate a test by applying a sample to a test strip, as shown in a step 1002. After the sample has been dosed, the test meter applies a first test voltage $V_1$ for a first time interval $t_1$, as shown in a step 1004a. A resulting test current is then measured for the first time interval $t_1$, as shown in a step 1005a. During the first time interval $t_1$, the test meter can perform a double dose check 1006a and a maximum current check 1012a. If either the double dose check 1006a or maximum current check 1012a fails, then the test meter will display an error message, as shown in a step 1028. If the double dose check 1006a and maximum current check 1012a both pass, then the test meter can apply a second test voltage $V_2$ for a second time interval $t_2$, as shown in a step 1004b.

A resulting test current is measured for the second time interval $t_2$, as shown in a step 1005b. During the application of the second test voltage $V_2$, the test meter can perform a sufficient volume check 1030, a double dose check 1006b, a maximum current check 1012b, and a minimum current check 1014b. If one of the checks 1030, 1006b, 1012b, or 1014b fails, then the test meter will display an error message, as shown in step 1028. If all of the checks 1030, 1006b, 1012b, and 1014b pass, then the test meter will apply a third test voltage $V_3$, as shown in a step 1004c.

A resulting test current is measured for the third time interval $t_3$, as shown in a step 1005c. During the application of the third test voltage $V_3$, the test meter can perform a double dose check 1006c, maximum current check 1012c, a minimum current check 1014c, a high resistance check 1022c, and a sample leakage check 1024c. If all of the checks 1006c, 1012c, 1014c, 1022c, and 1024c pass, then the test meter will display a glucose concentration, as shown in a step 1026. If one of the checks 1006c, 1012c, 1014c, 1022c, and 1024c fails, then the test meter will display an error message, as shown in step 1028. The following will describe the system checks and how errors can be identified using such system checks.

Sufficient Volume Check

In one embodiment for performing a sufficient volume check, a capacitance measurement is used. The capacitance measurement can measure essentially an ionic double-layer capacitance resulting from the formation of ionic layers at the electrode-liquid interface. A magnitude of the capacitance can be proportional to the area of an electrode coated with sample. Once the magnitude of the capacitance is measured, if the value is greater than a threshold and thus the test strip has a sufficient volume of liquid for an accurate measurement, a glucose concentration can be outputted, but if the value is not greater than a threshold and thus the test strip has an insufficient volume of liquid for an accurate measurement, then an error message can be outputted.

By way of non-limiting example, methods and mechanisms for performing capacitance measurements on test strips can be found in U.S. Pat. Nos. 7,195,704 and 7,199,594, each of which is hereby incorporated by reference in its entirety. In one method for measuring capacitance, a test voltage having a constant component and an oscillating component is applied to the test strip. In such an instance, the resulting test current can be mathematically processed, as described in further detail below, to determine a capacitance value.

Generally, when a limiting test current occurs at a working electrode having a well-defined area (i.e., an area not changing during the capacitance measurement), the most accurate and precise capacitance measurements in an electrochemical test strip can be performed. A well-defined electrode area that does not change with time can occur when there is a tight seal between the electrode and the spacer. The test current is relatively constant when the current is not changing rapidly due either to glucose oxidation or electrochemical decay. Alternatively, any period of time when an increase in signal, which would be seen due to glucose oxidation, is effectively balanced by a decrease in signal, which accompanies electrochemical decay, can also be an appropriate time interval for measuring capacitance.

An area of first electrode 166 can potentially change with time after dosing with the sample if the sample seeps in between the spacer 60 and the first electrode 166. In an embodiment of a test strip, reagent layer 72 can be have an area larger than the cutout area 68 that causes a portion of the reagent layer 72 to be in between the spacer 60 and the first electrode layer 66. Under certain circumstances, interposing a portion of the reagent layer 72 in between the spacer 60 and the first electrode layer 66 can allow the wetted electrode area to increase during a test. As a result, a leakage can occur during a test that causes the area of the first electrode to increase with time, which in turn can distort a capacitance measurement.

In contrast, an area of the second electrode 164 can be more stable with time compared to the first electrode 166 because there is no reagent layer in between the second electrode 164 and the spacer 60. Thus, the sample is less likely to seep in between the spacer 60 and the second electrode 164. A capacitance measurement that uses a limiting test current at the second electrode 164 can thus be more precise because the area does not change during the test.

Referring back to FIG. 6, once liquid is detected in the test strip, a first test voltage $V_1$ (e.g., -20 mV) can be applied between the electrodes for about 1 second to monitor the fill behavior of the liquid and to distinguish between control solution and blood. In Equation 1, the test currents are used from about 0.05 to 1 second. This first test voltage $V_1$ can be relatively low (i.e., the test voltage is similar in magnitude to the redox potential of the mediator) such that the distribution of ferrocyanide in the cell is disturbed as little as possible by the electrochemical reactions occurring at the first and second electrodes.

A second test voltage $V_2$ (e.g., -300 mV) having a larger absolute magnitude can be applied after the first test voltage $V_1$ such that a limiting current can be measured at the second electrode 164. The second test voltage $V_2$ can include an AC voltage component and a DC voltage component. The AC voltage component can be applied at a predetermined amount of time after the application of the second test voltage $V_2$, and further, can be a sine wave having a frequency of about 109 Hertz and an amplitude of about +/-50 millivolts. In a preferred embodiment, the predetermined amount of time can range from about 0.3 seconds to about 0.4 seconds after the application of the second test voltage $V_2$. Alternatively, the predetermined amount of time can be a time where a test current transient as a function of time has a slope of about zero. In another embodiment, the predetermined amount of time can be a time required for a peak current value (e.g., $i_{pb}$) to decay by about 50%. As for the DC voltage, it can be applied at a beginning of the first test voltage. The DC voltage component can have a magnitude sufficient to cause a limiting test current at the second electrode such as, for example, about -0.3 volts with respect to the second electrode.

Consistent with FIG. 4B, the reagent layer 72 is not coated onto the second electrode 164, which causes the magnitude of the absolute peak current $i_{pb}$ to be relatively low compared to the magnitude of the absolute peak current $i_{pc}$. The reagent layer 72 can be configured to generate a reduced mediator in a presence of an analyte, and the amount of the reduced mediator proximate to first electrode can contribute to the relatively high absolute peak current $i_{pc}$. In one embodiment at least the enzyme portion of the reagent layer 72 can be configured to not substantially diffuse from the first electrode to the second electrode when a sample is introduced into the test strip.

The test currents after $i_{pb}$ tends to settle to a flat region at approximately 1.3 seconds, and then the current increases again as the reduced mediator generated at the first electrode 166, which can be coated with the reagent layer 72, diffuses to the second electrode 164, which is not coated with the reagent layer 72. Generally, the glucose algorithm requires test current values both before and after the test interval of about 1.3 to about 1.4 seconds. For example, $i_{pb}$ is measured at 1.1 seconds in Equation 7 and test currents are measured at 1.4 seconds onwards for $$i_3 == \sum_{t=1.4}^{4} i(t).$$

In one embodiment, a capacitance measurement can be performed at a relatively flat region of the test current values, which can be performed at about 1.3 seconds to about 1.4 seconds. Generally, if the capacitance is measured before 1 second, then the capacitance measurement can interfere with the relatively low first test voltage $V_1$ that can be used in the CS/blood discrimination test 1806. For example, an oscillating voltage component on the order of +/-50 mV superimposed onto a -20 mV constant voltage component can cause significant perturbation of the measured test current. Not only does the oscillating voltage component interfere with the first test voltage $V_1$, but it can also significantly perturb the test currents measured after 1.4 seconds, which in turn can interfere with the blood glucose algorithm 1810. Following a great deal of testing and experimentation, it was finally determined that, surprisingly, measuring the capacitance at about 1.3 seconds to about 1.4 seconds resulted in accurate and precise measurements that did not interfere with the CS/blood discrimination test or the glucose algorithm.

After the second test voltage $V_2$, the third test voltage $V_3$ (e.g., +300 mV) can be applied causing the test current to be measured at the first electrode 166, which can be coated with the reagent layer 72. The presence of a reagent layer on the first electrode can allow penetration of liquid between the spacer layer and the electrode layer, which can cause the electrode area to increase.

As illustrated in FIG. 6, in an exemplary embodiment a 109 Hz AC test voltage (±50 mV peak-to-peak) can be applied for 2 cycles during the time interval $t_{cap}$. The first cycle can be used as a conditioning pulse and the second cycle can be used to determine the capacitance. The capacitance estimate can be obtained by summing the test current over a portion of the alternating current (AC) wave, subtracting the direct current (DC) offset, and normalizing the result using the AC test voltage amplitude and the AC frequency. This calculation provides a measure of the capacitance of the strip, which is dominated by the strip sample chamber when it is filled with a sample.

In one embodiment the capacitance can be measured by summing the test current over one quarter of the AC wavelength on either side of the point in time where the input AC voltage crosses the DC offset, i.e. when the AC component of the input voltage is zero (the zero crossing point). A derivation of how this translates to a measure of the capacitance is described in further detail below. Equation 20 can show the test current magnitude as a function of time during the time interval $t_{cap}$:

$$i(t) = i_o + st + I\sin(\omega t + \phi) \qquad \text{Eq. 20}$$

where the terms $i_o + st$ represent the test current caused by the constant test voltage component. Generally, the DC current component is considered as changing linearly with time (due to the on-going glucose reaction generating ferrocyanide) and is thus represented by a constant $i_o$, which is the DC current at time zero (the zero crossing point), and s, the slope of the DC current change with time. The AC current component is represented by $I\sin(\omega t + \phi)$, where I is the amplitude of the current wave, $\omega$ is its frequency, and $\phi$ is its phase shift relative to the input voltage wave. The term w can also be expressed as $2\pi f$, where f is the frequency of the AC wave in Hertz. The term I can also be expressed as shown in Equation 21:

$$I = \frac{V}{|Z|} \qquad \text{Eq. 21}$$

where V is the amplitude of the applied voltage signal and $|Z|$ is the magnitude of the complex impedance. The term $|Z|$ can also be expressed as shown in Equation 22:

$$|Z| = \frac{R}{\sqrt{1+\tan^2\phi}} = \frac{R}{\sqrt{1+\omega^2 R^2 C^2}} \qquad \text{Eq. 22}$$

where R is the real part of the impedance and C is the capacitance.

Equation 20 can be integrated from one quarter wavelength before the zero crossing point to one quarter wavelength after the zero crossing point to yield Equation 23:

$$\int_{-1/4f}^{1/4f} i(t) = i_o[t]_{-1/4f}^{1/4f} + \frac{s}{2}[t^2]_{-1/4f}^{1/4f} + I\int_{-1/4f}^{1/4f}\sin(\omega t + \phi), \qquad \text{Eq. 23}$$

which can be simplified to Equation 24:

$$\int_{-1/4f}^{1/4f} i(t) = \frac{i_o}{2f} + \frac{I\sin\phi}{\pi f} \qquad \text{Eq. 24}$$

By substituting Eq. 21 into Eq. 20, then into Eq. 23, and then rearranging, Equation 25 results:

$$C = \frac{1}{2V}\left(\int_{-1/4f}^{1/4f} i(t) - \frac{i_o}{2f}\right) \qquad \text{Eq. 25}$$

The integral term in Equation 25 can be approximated using a sum of currents shown in Equation 26:

$$\int_{-1/4f}^{1/4f} i(t) \approx \frac{\frac{1}{n}\sum_{k=1}^{n} i_k}{2f} \qquad \text{Eq. 26}$$

where the test currents $i_k$ are summed from one quarter wavelength before the zero crossing point to one quarter wavelength past the zero crossing point. Substituting Equation 26 into Equation 25 yields Equation 27:

$$C = \frac{\frac{1}{n}\sum_{k=1}^{n} i_k - i_0}{4Vf}, \qquad \text{Eq. 27}$$

in which the DC offset current $i_o$ can be obtained by averaging the test current over one full sine cycle around the zero crossing point.

In another embodiment, the capacitance measurements can be obtained by summing the currents not around the voltage zero crossing point, but rather around the maximum AC component of the current. Thus, in Equation 26, rather than sum a quarter wavelength on either side of the voltage zero crossing point, the test current can be summed a quarter wavelength around the current maximum. This is tantamount to assuming that the circuit element responding to the AC excitation is a pure capacitor, so $\phi$ is $\pi/2$. Thus, Equation 24 can be reduced to Equation 28:

$$\int_{-1/4f}^{1/4f} i(t) = \frac{i_o}{2f} + \frac{I}{\pi f} \qquad \text{Eq. 28}$$

This is a reasonable assumption in this case as the uncoated electrode is polarized such that the DC, or real, component of the current flowing is independent of the voltage applied over the range of voltages used in the AC excitation. Accordingly, the real part of the impedance responding to the AC excitation is infinite, implying a pure capacitive element. Equation 28 can then be used with Equation 25 to yield a simplified capacitance equation that does not require an integral approximation. The net result is that capacitance measurements when summing the currents not around the voltage crossing point, but rather around the maximum AC component of the current, were more precise.

In one exemplary embodiment the microprocessor of the test meter can have a heavy load with calculating the glucose concentration. In such an instance, because the capacitance data acquisition needs to be made part way through the test rather than at its beginning, it can be necessary to defer the processing of the capacitance measurement data until after the determination of the glucose concentration is completed. Thus, once the glucose measurement part of the test is completed, the capacitance can be calculated, and if the capacitance is below a pre-determined threshold, a partial fill error can be flagged.

Under certain circumstances the capacitance measurement can depend on the environmental temperature. To measure capacitance in an accurate and precise manner for determining electrode fill volumes, the effect of temperature can be reduced using a temperature correction for blood as shown in Equation 29:

$$Cap_{corr} = Cap - 1.9 \times T \qquad \text{Eq. 29}$$

where $Cap_{corr}$ is i the temperature corrected capacitance value, Cap is capacitance, and T is temperature.

The effect of temperature can be removed using a temperature correction for CS as shown in Equation 30:

$$Cap_{corr} = Cap - 0.56 \times T \qquad \text{Eq. 30}$$

The temperature-corrected capacitance values from Equations 29 and 30 can be used for identifying partially filled test strips.

As illustrated by Table 1 below, a different temperature-corrected capacitance threshold value will be required for blood and control solution. The threshold should generally be set four (4) standard deviation units below the mean. Statistically this equates to a 99.994% certainty that no complete fill will be identified as a partial fill. The temperature-corrected capacitance threshold value for blood will be about 450 nF, and the corresponding value for control solution will be about 560 nF. These values can be programmed into a memory portion of the test meters. In an alternative embodiment, the threshold value can be adjusted by the operator depending on the intended use.

TABLE 1

Temperature-corrected capacitance values for complete fills

| Parameter | All bloods results | All CS results |
|---|---|---|
| Mean capacitance (nF) | 515 | 664 |
| SD (nF) | 16 | 27 |
| Mean −4*SD (nF) | 451 | 556 |

Figure 19:
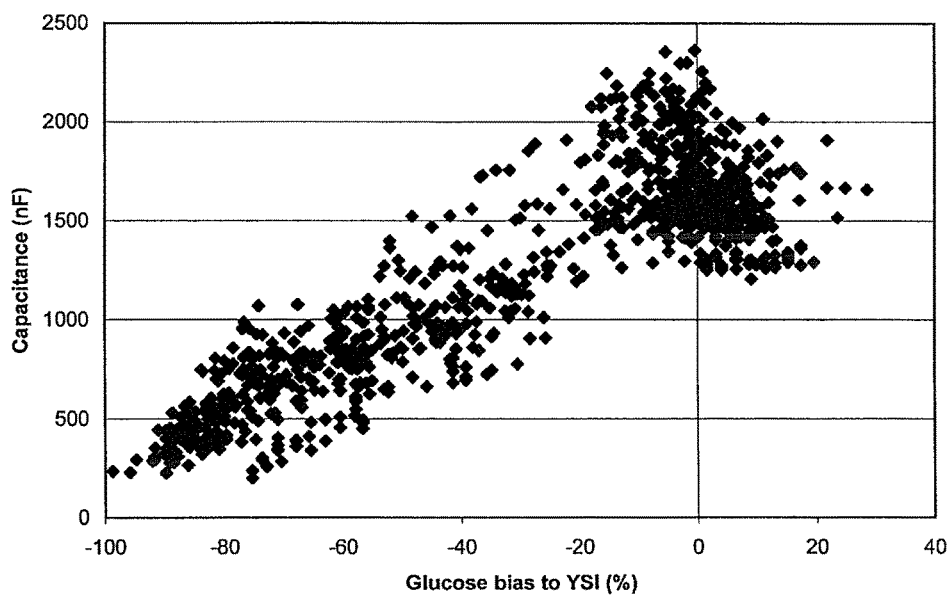
FIG. 19 is a chart showing a correlation of capacitance and bias to a reference glucose measurement (YSI, Yellow Springs Instrument) where capacitance values were measured for blood samples during the third test voltage of FIG. 6.

The chart of FIG. 19 shows a correlation of capacitance and bias to a reference glucose measurement (YSI, Yellow Springs Instrument). The measured glucose concentrations were converted to a bias by comparing it to a glucose measurement performed with a reference instrument. Several test strips were filled with various volumes of blood, and the capacitance and glucose concentrations were measured with the test voltage waveform of FIG. 6. More particularly, the capacitance was measured during the third test voltage $V_3$ where the test current is relatively large and decreases rapidly with time. Additionally, the capacitance measurements were performed where the limiting test current occurs on the first electrode, which has a reagent layer coating.

If it is assumed that the main contributor to the bias to YSI is caused by the percentage partial coverage of the electrodes with liquid, then the capacitance values should form a straight line with relatively little scatter when correlated to the YSI bias. For example, a 50% negative bias to YSI should correspond to a 50% decrease in capacitance compared to a fully-filled test strip. Thus, if it is also assumed that the strip-to-strip variation in bias is relatively small, then the relatively large scatter of data points in FIG. 19 can be ascribed to a relatively large variation in the capacitance measurements. It was found that capacitance variation was caused by performing the capacitance measurement during the third test voltage where the test current values are generally not relatively constant.

A relatively large scatter in the capacitance measurements could cause a significant number of fully-filled test strips to be rejected. Further, a large capacitance variation can cause some capacitance measurements to be biased low, and thus, be below a sufficiently filled threshold resulting in a falsely identified partial fill.

The chart of FIG. 20 shows a correlation of capacitance (measured at about 1.3 seconds) and bias to a reference glucose measurement (YSI, Yellow Springs Instrument). Several test strips were filled with various volumes of blood, and the capacitance and glucose concentrations were measured with the test voltage waveform of FIG. 6. More particularly, the capacitance was measured during the second test voltage $V_2$ where the test current is relatively constant. In addition, the capacitance measurement was performed where the limiting test current occurs on the second electrode, which did not have a reagent layer coating. In contrast to FIG. 19, the data in FIG. 20 shows that the capacitance values are less scattered.

Figure 21:
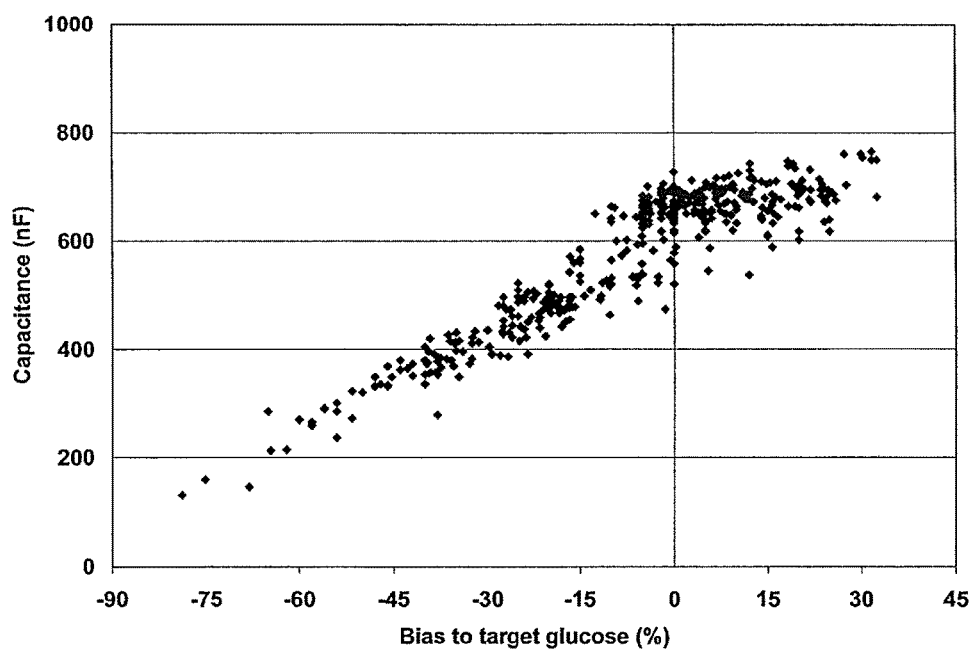
FIG. 21 is a chart showing a correlation of capacitance and bias to a reference glucose measurement (YSI, Yellow Springs Instrument) where capacitance values were measured for control solution samples during the second test voltage of FIG. 6 (e.g., after approximately 1.3 seconds)

The chart of FIG. 21 shows a correlation of capacitance (measured at about 1.3 seconds) and bias to a reference glucose measurement (YSI, Yellow Springs Instrument). Several test strips were filled with various volumes of CS, and the capacitance and glucose concentrations were measured with the test voltage waveform of FIG. 6. Similar to FIG. 20, the data in FIG. 21 shows that the capacitance values have a relatively low amount of variation when performed during this time interval.

Double-Dosing Events

Figure 22:
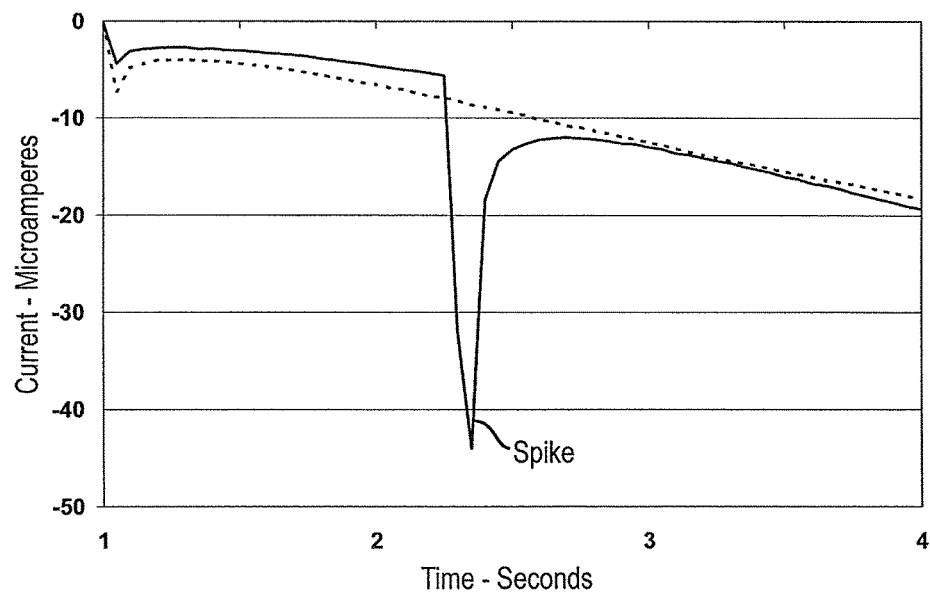
FIG. 22 shows a test current transient of the second test time interval when a user performs a double dose (solid line) and does not perform a double dose (dotted line)

A double dose occurs when a user applies an insufficient volume of blood to a sample-receiving chamber and then applies a subsequent bolus of blood to further fill the sample-receiving chamber. An insufficient volume of blood expressed on a user's fingertip or a shaky finger can cause the occurrence of a double-dosing event. The currently disclosed system and method can be configured to identify such double-fill events. For example, FIG. 22 shows a test current transient where a user performed a double-dosing event during the second test time interval $t_2$ that caused a spike to be observed (see solid line). When there is no double-dosing event, the test current transient does not have a peak (see dotted line of FIG. 22).

A double-dosing event can cause a glucose test to have an inaccurate reading. Thus, it is usually desirable to identify a double-dosing event and then have the meter output an error message instead of outputting a potentially inaccurate reading. A double-dosing event initially causes the measured test current to be low in magnitude because the electrode area is effectively decreased when only a portion is wetted with sample. Once the user applies the second dose, a current spike will occur because of a sudden increase in the effective electrode area and also because turbulence causes more reduced mediator to be transported close to the working electrode. In addition, less ferrocyanide will be generated because a portion of the reagent layer is not wetted by sample for the entire test time. Thus, an inaccurate glucose reading can result if a test current value used in the glucose algorithm is depressed or elevated as a result of the double-dosing.

A method of identifying a double-dosing event (1006a, 1006b, or 1006c) may include measuring a second test current and a third test current where the second test current occurs before the third test current. An equation may be used to identify double-dosing events based on a difference between the absolute value of the third test current and the absolute value of the second test current. If the difference is greater than a predetermined threshold, the test meter may output an error message indicative of a double-dosing event. The method of identifying the double-dosing event may be performed multiple times in serial manner as the test current values are collected by the test meter. The equation can be in the form of Equation 31 for calculating a difference value $Z_2$ for determining whether a double-dosing event had occurred:

$$Z_2 = \text{abs}(i(t+x)) - \text{abs}(i(t))$$

where i(t) is a second test current, i(t+x) is a third test current, t is a time for the second test current, and x is an increment of time in between current measurements. If the value $Z_2$ is greater than a predetermined threshold of about three (3) microamperes, then the test meter may output an error message due to a double-dosing event. The predetermined thresholds disclosed herein are illustrative for use with test strip 100 and with the test voltage waveform of FIG. 6 where working electrode and reference electrode both have an area of about 0.042 cm$^2$ and a distance between the two electrodes ranging from about 90 microns to about 100 microns. It should be obvious to one skilled in the art that such predetermined thresholds may change based on the test strip design, the test voltage waveform, and other factors.

In another embodiment for identifying a double-dosing event (e.g., 1006a, 1006b, or 1006c), a method may include measuring a first test current, a second test current, and third test current where the first test current occurs before the second test current and the third test current occurs after the second test current. An equation may be used to identify double-dosing events based on two times the absolute value of the second test current minus the absolute value of first test current and minus the absolute value of the third test current. The equation may be in the form of Equation 32 for calculating a summation value Y for determining whether a double-dosing event had occurred:

$$Y = 2*\text{abs}(i(t)) - \text{abs}(i(t-x)) - \text{abs}(i(t+x))$$

where i(t) is a second test current, i(t-x) is a first test current, i(t+x) is a third test current, t is a time for the second test current, and x is an increment of time in between measurements, and abs represents an absolute function. If the summation value Y is greater than a predetermined threshold, then the test meter may output an error message due to a double-dosing event. The predetermined threshold may be set to a different value for the first time interval $t_1$, second time interval $t_2$, and third time interval $t_3$.

In one embodiment the predetermined threshold may be about two (2) microamperes for the first time interval $t_1$, about two (2) microamperes for the second time interval $t_2$, and about three (3) microamperes for the third time interval $t_3$. The predetermined thresholds may be adjusted as a result of the following factors such as noise in the test meter, frequency of test current measurements, the area of the electrodes, the distance between the electrodes, the probability of a false positive identification of a double-dosing event, and the probability of a false negative identification of a double-dosing event. The method of identifying the double-dosing event using Equation 32 can be performed for multiple portions of the test current transient. It should be noted that Equation 32 can be more accurate than Equation 31 for identifying double-dosing events because the first test current and third test current provide a baseline correction. When using the test voltage waveform of FIG. 6, the double-dosing check can be performed at a time period just after the beginning of the first, second, and third time intervals because a peak typically occurs at the beginning of the time intervals. For example, the test currents measured at zero seconds to about 0.3, 1.05, and 4.05 seconds should be excluded from the double-dosing check.

Maximum Current Check

Figure 23:
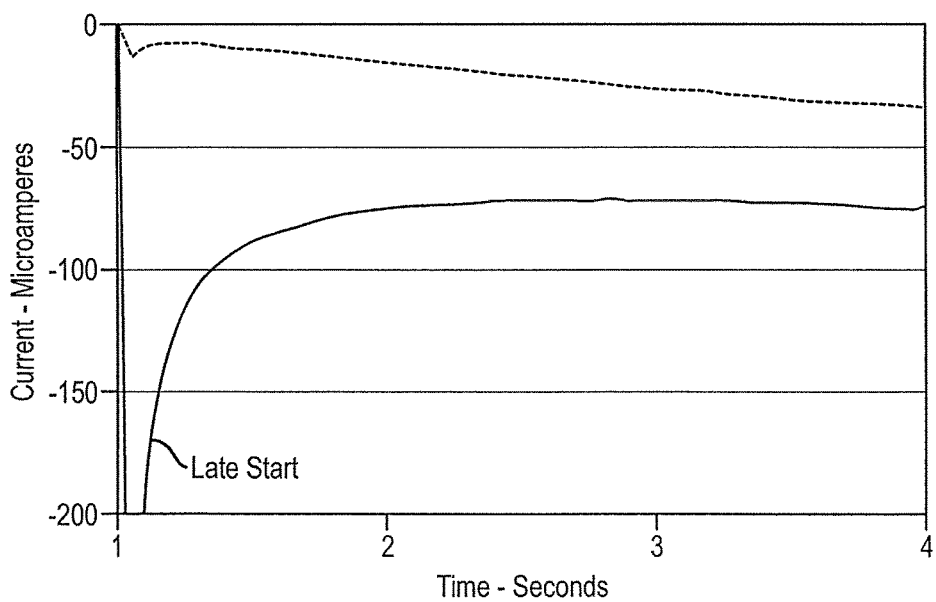
FIG. 23 shows a test current transient of the second test time interval when a late start error occurs (solid line) and does not occur (dotted line) with the test meter.

As referred to in steps 1012a, 1012b, and 1012c of FIG. 18, a maximum current check can be used to identify a test meter error or a test strip defect. An example of a test meter error occurs when the blood is detected late after it is dosed. An example of a defective test strip occurs when the first and second electrode are shorted together. FIG. 23 shows a test current transient where the test meter did not immediately detect the dosing of blood into the test strip (see solid line). In such a scenario, a late start will generate a significant amount of ferrocyanide before the second test voltage $V_2$ is applied causing a relatively large test current value to be observed. In contrast, when the test meter properly initiates the test voltage waveform once blood is applied, the test current values for the second time interval are much smaller, as illustrated by the dotted line in FIG. 23.

A late start event can cause an inaccurate glucose reading. Thus, it would be desirable to identify a late start event and then have the meter output an error message instead of outputting an inaccurate reading. A late start event causes the measured test current to be larger in magnitude because there is more time for the reagent layer to generate ferrocyanide. Thus, the increased test current values will likely distort the accuracy of the glucose concentration.

In addition to a test meter error, a short between the first and second electrode can cause the test current to increase. The magnitude of this increase depends on the magnitude of the shunting resistance between the first and second electrode. If the shunting resistance is relatively low, a relatively large positive bias will be added to the test current causing a potentially inaccurate glucose response.

Maximum current check (1012a, 1012b, and 1012c) can be performed by comparing the absolute value of all of the measured test current values to a predetermined threshold and outputting an error message if the absolute value of one of the measured test current values is greater than the predetermined threshold. The predetermined threshold can be set to a different value for the first, second, and third test time intervals ($t_1$, $t_2$, and $t_3$). In one embodiment, the predetermined threshold may be about 50 microamperes for the first time interval $t_1$, about 300 microamperes for the second time interval $t_2$, and about 3000 microamperes for the third time interval $t_3$.

Maximum Current Check:

As referred to in steps 1014b and 1014c of FIG. 18, a minimum current check can be used to identify a false start of a glucose test, an improper time shift by a test meter, and a premature test strip removal. A false start can occur when the test meter initiates a glucose test even though no sample has been applied to the test strip. Examples of situations that can cause a test meter to inadvertently initiate a test are an electrostatic discharge event (ESD) or a temporary short between first and second electrodes. Such events can cause a relatively large current to be observed for a least a short moment in time that initiates a test even though no liquid sample has been introduced into the test strip.

An inadvertent initiation of a glucose test can cause a test meter to output a low glucose concentration even though no sample has yet been applied to the test strip. Thus, it would be desirable to identify an inadvertent initiation of a glucose test so that the test meter does not output a falsely low glucose reading. Instead, the test meter should provide an error message that instructs the user to re-insert the same test strip or to insert a new test strip for performing the test again.

A time shifting error by the test meter can occur when the third test voltage $V_3$ is applied early or late. An early application of the third test voltage $V_3$ should cause the test current value at the end of the second time interval $t_2$ to be a relatively large current value with a positive polarity instead of a relatively small current value with a negative polarity. A late application of the third test voltage $V_3$ should cause the test current value at the beginning of the third time interval to be a relatively small current value with a negative polarity instead of a relatively large current value with a positive polarity. For both the early and late application of the third test voltage $V_3$, there is a possibility of causing an inaccurate glucose result. Therefore, it would be desirable to identify a time shifting error by the test meter using the minimum current check so that an inaccurate glucose reading does not occur.

A premature removal of a test strip from the test meter before the end of a glucose test can also cause an inaccurate glucose reading to occur. A test strip removal would cause the test current to change to a value close to zero potentially causing an inaccurate glucose output. Accordingly, it would also be desirable to identify a premature strip removal using a minimum current check so that an error message can be provided instead of displaying an inaccurate glucose reading.

The minimum current check may be performed by comparing the absolute value of all of the measured test current values during the second and third time intervals ($t_2$ and $t_3$) to a predetermined threshold and outputting an error message if the absolute value of one of the measured test current values is less than a predetermined threshold. The predetermined threshold may be set to a different value for the second and third test time intervals. However, in one embodiment, the predetermined threshold may be about 1 microampere for the first time interval $t_1$ and the second time interval $t_2$. Note that the minimum current check was not performed for the first time interval because the test current values are relatively small because the first test voltage $V_1$ is close in magnitude to the redox potential of the mediator.

High Resistance Track:

As referred to in step 1022c of FIG. 18, a high resistance track can be detected on a test strip that can result in an inaccurate glucose reading. A high resistance track can occur on a test strip that has an insulating scratch or a fouled electrode surface. For the situation in which the electrode layers are made from a sputtered gold film or sputtered palladium film, scratches can easily occur during the handling and manufacture of the test strip. For example, a scratch that runs from one lateral edge 56 to another lateral edge 58 on first electrode layer 66 can cause an increased resistance between first contact pads 67 and first electrode 166. Sputtered metal films tend to be very thin (e.g., 10 to 50 nm) making them prone to scratches during the handling and manufacture of the test strip. In addition, sputtered metal films can be fouled by exposure to volatile compounds such as hydrocarbons. This exposure causes an insulating film to form on the surface of the electrode, which increases the resistance. Another scenario that can cause a high resistance track is when the sputtered metal film is too thin (e.g., <<10 nm). Yet another scenario that can cause a high resistance track is when the test meter connectors do not form a sufficiently conductive contact to the test strip contact pads. For example, the presence of dried blood on the test meter connectors can prevent a sufficiently conductive contact to the test strip contact pads.

Figure 24:
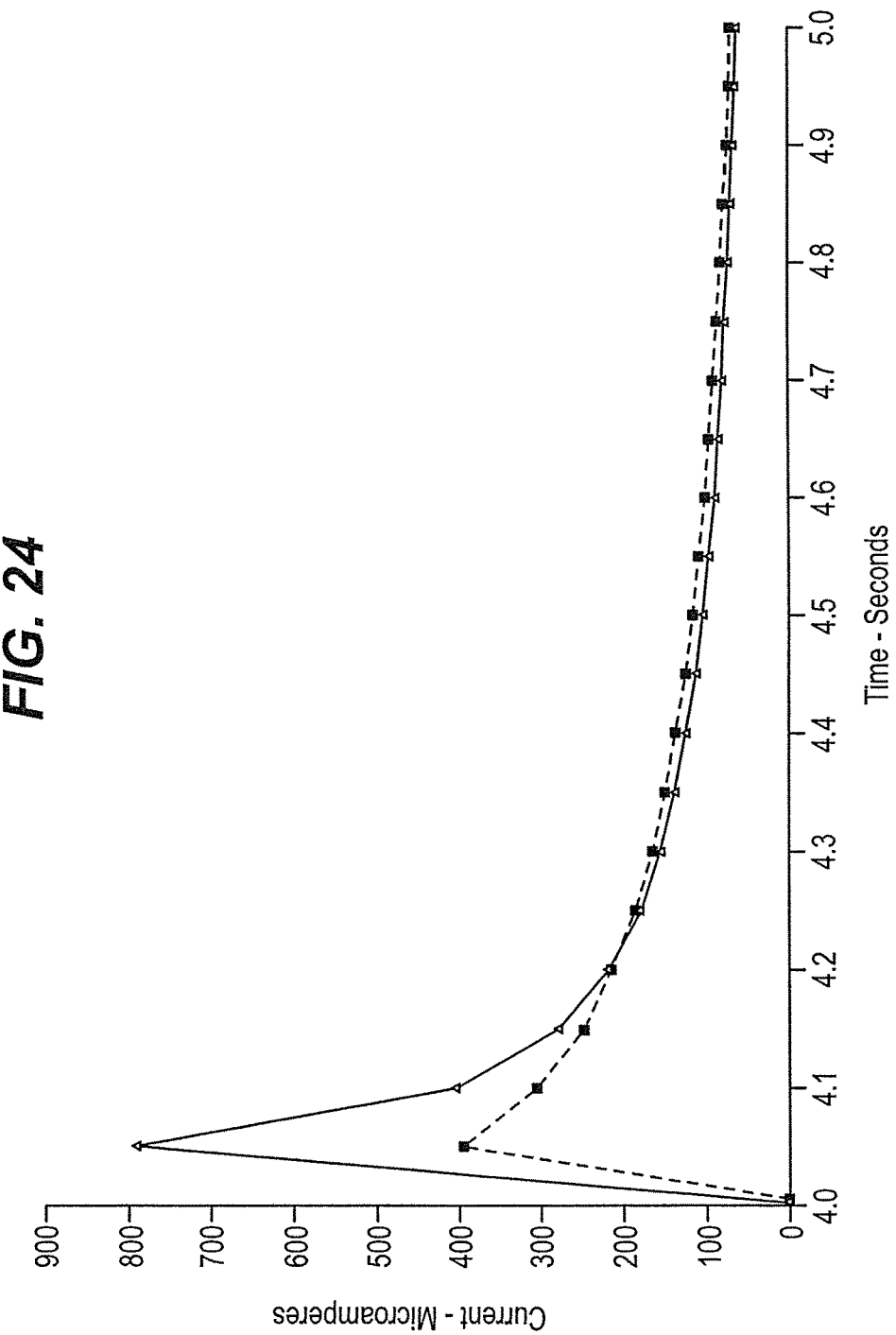
FIG. 24 shows a test current transient of the third test time interval for a test strip having a high resistance track (squares) and a low resistance track (triangles)

FIG. 24 shows two test current transients during a third time interval $t_3$ for a test strip having a high resistance track (squares) and a low resistance track (triangles). A sufficiently high track resistance R that is between the electrode and the electrode contact pad can substantially attenuate the magnitude of the effectively applied test voltage $V_{eff}$ which in turn can attenuate the magnitude of the resulting test current. The effective test voltage $V_{eff}$ can be described by Equation 33:

$$V_{eff} = V - i(t)R$$

Generally, $V_{eff}$ will be the most attenuated at the beginning of the third time interval $t_3$ where the test current will generally have the highest magnitude. The combination of a relatively large R and a relatively large test current at the beginning of the third time interval $t_3$ can cause a significant attenuation in the applied test voltage. In turn, this could cause an attenuation of the resulting test current at the beginning of the third time interval $t_3$, as illustrated in FIG. 24 at t=4.05 seconds. Such attenuation in the peak current immediately at about 4.05 seconds can cause the calculated glucose concentration to be inaccurate. In order to avoid significant attenuation in the applied test voltage, R should be a relatively small value (i.e., low track resistance). In one embodiment, a low resistance track may be represented by an electrode layer having a resistivity of less than about 12 ohms per square and a high resistance track may be represented by an electrode layer having a resistivity of greater than about 40 ohms per square.

A determination of whether a test strip has a high track resistance can use an equation based on a first test current $i_1$ and a second test current $i_2$ that both occur during the third time interval $t_3$. The first test current $i_1$ may be measured at about a beginning of the third time interval $t_3$ (e.g., 4.05 seconds) where the magnitude is at a maximum or close to the maximum. The second test current $i_2$ may be measured at about an end of the third time interval $t_3$ (e.g., 5 seconds) where the magnitude is at the minimum or close to the minimum.

The equation for identifying a high track resistance may be in the form of Equation 34:

$$R_1 = \frac{i_1}{i_1 - i_2} \qquad \text{Eq. 34}$$

If first ratio $R_1$ is greater than a predetermined threshold, then the test meter may output an error message due to the test strip having a high resistance track. The predetermined threshold may be about 1.2. It is significant that the first test current $i_1$ is about a maximum current value because it is the most sensitive to resistance variations according to Equation 33. If a first test current $i_1$ is measured at a time that was closer to the minimum current value, then Equation 34 would be less sensitive for determining whether a high resistance track was present. It is advantageous to have relatively low variation in the first ratio $R_1$ when testing low resistance test strips. The relatively low variation decreases the likelihood of mistakenly identifying a high resistance track test strip. As determined and described herein, the variation of first ratio $R_1$ values for test strips having a low resistance track is about four times lower when a first test current value $i_1$ was defined as a current value immediately after the application of the third test voltage $V_3$, as opposed to being a sum of current values during the third time interval $t_3$. When there is a high variation in first ratio $R_1$ values for low resistance test strips, the probability of mistakenly identifying a high resistance track increases.

Figure 25:
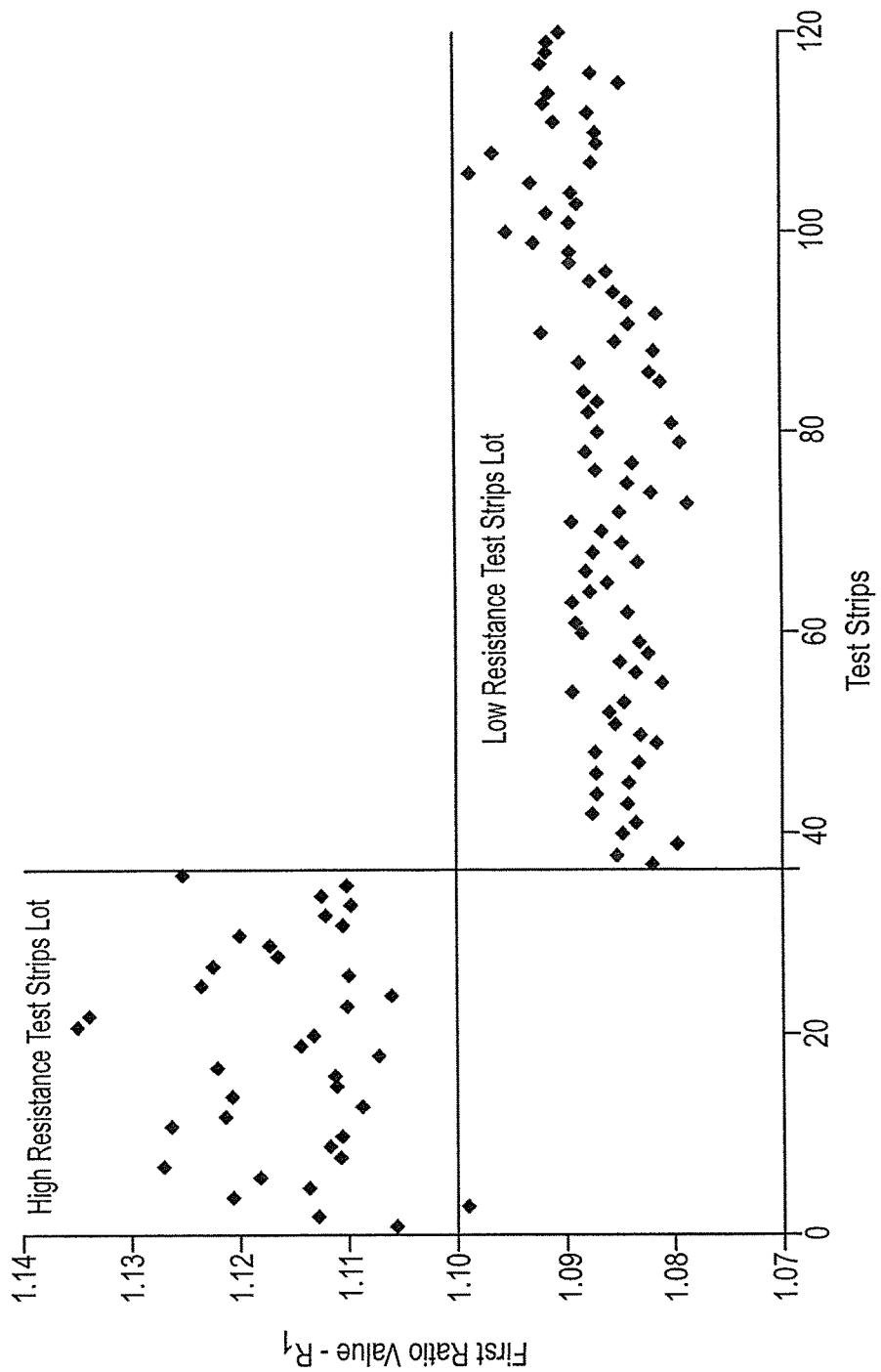
FIG. 25 is a chart showing a plurality of ratio values indicating that a high resistance test strip lot can be distinguished from a low resistance test strip lot.

FIG. 25 is a chart showing a plurality of $R_1$ values calculated with Equation 34 for two test strip lots where one lot has a high resistance track and the other lot has a low resistance track. One lot of test strip was purposely manufactured with a high resistance track by using palladium electrodes that were purposely fouled by an exposure to gas containing hydrocarbons for several weeks. The second test strip lot was manufactured without purposely fouling the electrode surface. To prevent fouling, a roll of sputtered coated palladium was coated with MESA before coating with the reagent layer. All of the low resistance test strips which were not fouled, had $R_1$ values of less than 1.1 indicating that Equation 34 could identify low track resistance test strips. Similarly, essentially all of the high resistance test strips, which were purposely fouled, had $R_1$ values of greater than 1.1 indicating that Equation 34 could identify high track resistance test strips.

Leakage

Figure 26:
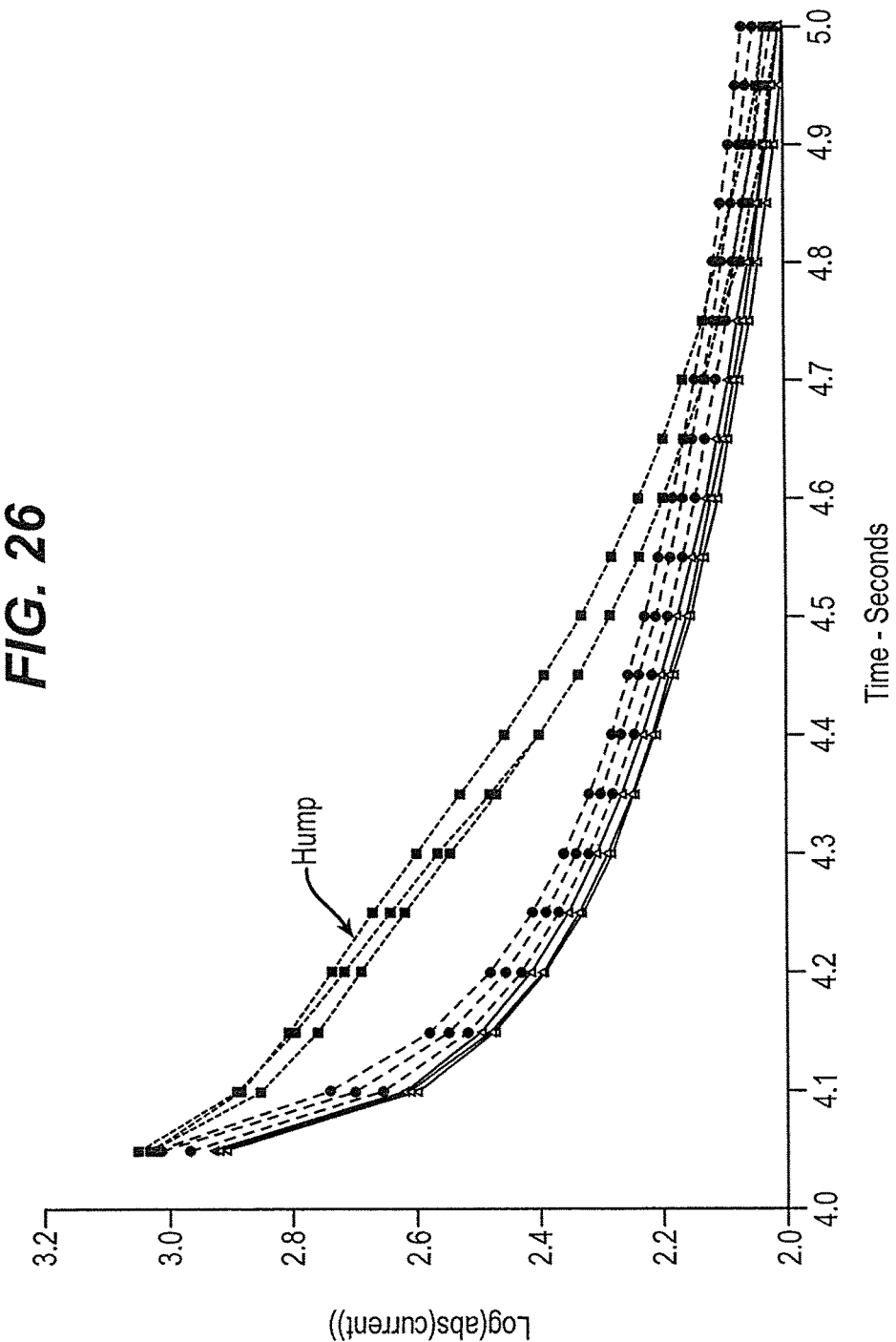
FIG. 26 shows a plurality of test current transients for a test strip lot having leakage between a spacer and the first electrode (squares) and for test strip lots having a sufficiently low amount of leakage (circles and triangles)

As previously referred to in step 1024c in FIG. 18, a leakage can be detected on a test strip when the spacer 60 does not form a sufficiently strong liquid impermeable seal with the first electrode layer 66. A leakage occurs when liquid seeps in between the spacer 60 and the first electrode 166 and/or the second electrode 164. Note that FIG. 4B shows a reagent layer 72 that is immediately adjacent to the walls of the spacer 60. However, in another embodiment (not shown) where leakage is more likely to occur, the reagent layer 72 can be have an area larger than the cutout area 68 that causes a portion of the reagent layer 72 to be in between the spacer 60 and the first electrode layer 66. Under certain circumstances, interposing a portion of the reagent layer 72 in between the spacer 60 and the first electrode layer 66 can prevent the formation of a liquid impermeable seal. As a result, a leakage can occur which creates an effectively larger area on either the first electrode 166, which in turn, can cause an inaccurate glucose reading. An asymmetry in area between the first electrode 166 and the second electrode 164 can distort the test current transient where an extra hump appears during the third time interval $t_3$, as illustrated in FIG. 26.

FIG. 16 shows test current transients during a third time interval $t_3$ for three different types of test strip lots where test strip lot 1 (squares) has a leakage of liquid between the spacer and the first electrode. Test strip lot 1 was constructed using a dryer setting that did not sufficiently dry the reagent layer and also was laminated with a pressure setting that was not sufficient to form a liquid impermeable seal to the electrodes. Normally, the reagent layer is sufficiently dried so that an adhesive portion of the spacer 60 can intermingle with the reagent layer and still form a liquid impermeable seal to the first electrode layer 166. In addition, sufficient pressure must be applied so that the adhesive portion of the spacer 60 can form the liquid impermeable seal to the first electrode layer 166. The test strip lot 2 was prepared similarly to test strip lot 1 except that they were stored at about 37 degrees Celsius for about two weeks. The storage of the test strip lot 2 caused the spacer to reform creating a liquid impermeable seal to the electrodes. Test strip lot 3 was constructed using a dryer setting that was sufficient to dry the reagent layer and also was laminated with a pressure setting sufficient to form a liquid impermeable seal. Both test strip lots 2 and 3 (triangles and circles respectively) show a more rapid decay in the test current magnitude with time compared to test strip 1 (squares), as illustrated in FIG. 26.

A determination of whether a test strip leaks can be performed using an equation based on a first test current, a second test current, a third test current, and a fourth test current that occur during the third test time interval. A first logarithm of a second ratio can be calculated based on a first test current $i_1$ and a second test current $i_2$. A second logarithm of a third ratio can be calculated based on a third test current $i_3$ and a fourth test current $i_4$. An equation may be used to calculate a fourth ratio $R_4$ based on the first logarithm and the second logarithm. If the fourth ratio $R_4$ is less than a predetermined ratio, then the test meter will output an error message due to leakage. The predetermined threshold may range from about 0.95 to about 1. The equation for identifying leakage can be in the form of Equation 35:

$$R_4 = \frac{\log\left(\frac{i_1}{i_2}\right)}{\log\left(\frac{i_3}{i_4}\right)} \qquad \text{Eq. 35}$$

In one embodiment, the first test current $i_1$ and the second test $i_2$ current may be about the two largest current values occurring the third time interval $t_3$, the fourth test current $i_4$ may be a smallest current value occurring the third time interval $t_3$, and the third test current $i_3$ may be selected at a third test time so that a difference between the fourth test time and a third test time is greater than a difference between a second test time and a first test time. In one illustrative embodiment, the first test current, the second test current, the third test current, and the fourth test current may be measured at about 4.1 seconds, 4.2 seconds, 4.5 seconds, and 5 seconds, respectively.

Figure 27:
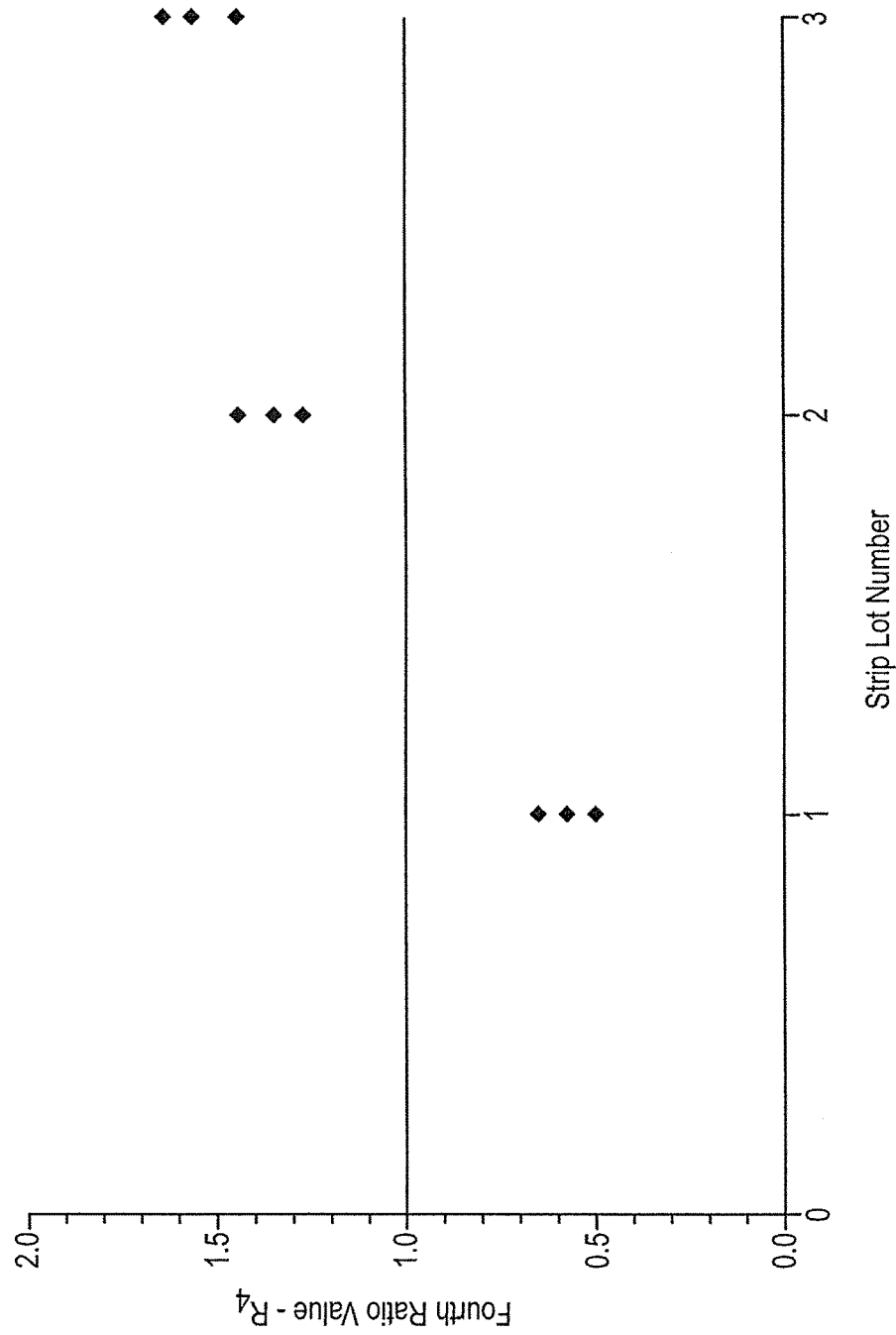
FIG. 27 is a chart showing a plurality of ratio values for identifying leakage of liquid for test strip lots prepared with different manufacturing conditions.

FIG. 27 is a chart showing a plurality of $R_4$ values calculated with Equation 35 for the three test strip lots described for FIG. 26. Accordingly, test strip lot 1 has fourth ratio values less than one and both test strip lots 2 and 3 have fourth ratio $R_4$ values greater than one indicating that Equation 35 can successfully identify strip leakages.

In an alternative embodiment, a determination of whether a test strip has a leakage can be performed using an equation based on only three test current values instead of using four test current values as shown in Equation 35. The three test current values may include a first test current $i_1$, a third test current $i_3$, and a fourth test current $i_4$ that all occur during the third test time interval $t_3$. A third logarithm of a fifth ratio may be calculated based on the first test current $i_1$ and the third test current $i_3$. A second logarithm of a third ratio may be calculated based on the third test current $i_3$ and the fourth test current $i_4$. An equation may be used to calculate a sixth ratio $R_6$ based on the third logarithm and the second logarithm. If $R_6$ is less than a predetermined ratio, then the test meter will output an error message due to leakage. The equation for identifying leakage may be in the form of Equation 36:

$$R_5 = \frac{\log\left(\frac{i_1}{i_3}\right)}{\log\left(\frac{i_3}{i_4}\right)}$$ Eq. 36

One skilled in the art will appreciate further features and advantages of the present disclosure based on the above-described embodiments. Accordingly, the present disclosure is not to be limited by what has been particularly shown and described, except as indicated by the appended claims. All publications and references cited herein are expressly incorporated herein by reference in their entirety.

The invention claimed is:

1. A method for determining whether a test strip is sufficiently filled with a sample and distinguishing the sample as a control solution or a physiological sample, the test strip comprising a first electrode and a second electrode, the first electrode being coated with a reagent layer and the second electrode not having a reagent layer coating, and the method comprising:

selecting a first DC test voltage and a first time interval, the first DC test voltage being selected to minimize disturbances of a distribution of a reduced mediator within the test strip, the reduced mediator being a reaction product of the sample and the reagent layer of the first electrode, wherein the first time interval is approximately 1 second;

applying the selected first DC test voltage between the first electrode and the second electrode of the test strip for the first time interval once liquid is detected in the test strip to distinguish between a control solution and a physiological sample;

measuring a capacitance value, the measuring comprising:

applying a second test voltage between the first electrode and the second electrode for a second time interval directly after the first voltage applying step, the second test voltage having a DC voltage component and a superimposed AC voltage component in which the DC voltage component has a larger absolute magnitude than the first DC test voltage, the AC voltage component being applied for only a predetermined time interval starting at a predetermined amount of time after the application of the first DC test voltage and the DC voltage component of the second test voltage, the DC voltage component having a magnitude sufficient to cause a limiting test current at the second electrode, wherein a wetted electrode area of the first electrode increases during the measuring and the second electrode not having the reagent layer coating facilitates measuring the capacitance value notwithstanding the increase of the wetted electrode area during the measuring, and wherein the second time interval is selected to allow sufficient time for distinguishing the sample as the control solution or the physiological sample without interference from the AC voltage and the predetermined amount of time of application of the AC voltage component after the application of the first DC test voltage and the DC voltage component of the second test voltage is selected to allow the sample to fill a sample-receiving chamber of the test strip and the reagent layer to at least partially dissolve before applying the AC voltage component and minimize perturbing a subsequent analyte concentration measurement;

processing a portion of the test currents, resulting from the AC voltage component, into the capacitance value in which a portion of the test currents, resulting from the AC voltage component and the DC voltage component of the second test voltage, are summed only between at about a ¼ wavelength before and about a ¼ wavelength after one of a zero voltage crossing point or a maximum AC voltage component; and utilizing the measured capacitance value to determine whether the test strip is sufficiently filled with the sample, by determining that the test strip is sufficiently filled with the sample if the measured capacitance value is greater than a predetermined threshold and determining that the test strip is not sufficiently filled with the sample if the capacitance value is less than a predetermined threshold.

2. The method of claim 1, in which the limiting test current is a limiting oxidation test current where substantially all of a reduced mediator has been depleted at a surface of the second working electrode.

3. The method of claim 1, in which a magnitude of the second test voltage is sufficient to oxidize a reduced mediator at the second electrode.

4. The method of claim 1, in which the DC voltage component is applied at a beginning of the second test voltage.

5. The method of claim 1, in which the DC voltage component is about −0.3 volts with respect to the second electrode.

6. The method of claim 1, in which the AC voltage component is a sine wave having a frequency of about 109 Hertz and an amplitude of about +/−50 millivolts.

7. The method of claim 1, in which the reagent layer coating is on the first electrode.

8. The method of claim 7, in which the reagent layer is configured to generate reduced mediator in a presence of an analyte.

9. The method of claim 8, in which the reagent layer comprises a mediator and an enzyme where the enzyme does not substantially diffuse from the first electrode to the second electrode when sample is introduced into the test strip.

10. The method of claim 8, in which the first electrode and the second electrode are in an opposing face format.

11. The method of claim 1, in which the predetermined amount of time ranges from about 0.3 seconds to about 0.4 seconds after the application of the first test voltage.

12. The method of claim 1, in which the predetermined amount of time is a time where a test current transient as a function of time has a slope of about zero.

13. The method of claim 1, in which the predetermined amount of time is a time required for a peak current value to decay by about 50%.

14. The method of claim 1, in which the predetermined time is not later than 1.4 seconds following the application of the first test voltage.

* * * * *